(12) United States Patent
Knill et al.

(10) Patent No.: US 8,785,205 B2
(45) Date of Patent: Jul. 22, 2014

(54) DETECTION OF NICOTINE METABOLITES

(75) Inventors: Charles John Knill, Tenbury Wells (GB); John Frederick Kennedy, Tenbury Wells (GB)

(73) Assignee: GFC Diagnostics Ltd., Oxon (GB)

( * ) Notice: Subject to any disclaimer, the term of this patent is extended or adjusted under 35 U.S.C. 154(b) by 0 days.

(21) Appl. No.: 13/697,446

(22) PCT Filed: May 13, 2011

(86) PCT No.: PCT/GB2011/000734
§ 371 (c)(1),
(2), (4) Date: Jan. 8, 2013

(87) PCT Pub. No.: WO2011/141712
PCT Pub. Date: Nov. 17, 2011

(65) Prior Publication Data
US 2013/0130396 A1    May 23, 2013

(30) Foreign Application Priority Data
May 13, 2010    (GB) .................................. 1008039.8

(51) Int. Cl.
*G01N 33/52*    (2006.01)
*G01N 33/50*    (2006.01)
*G01N 33/00*    (2006.01)
*G01N 33/94*    (2006.01)

(52) U.S. Cl.
CPC ............... *G01N 33/52* (2013.01); *G01N 33/94* (2013.01)
USPC ............................................... 436/96; 436/91

(58) Field of Classification Search
CPC ... G01N 33/00; G01N 33/94; G01N 33/9406; G01N 33/942; G01N 33/22; G01N 33/52; Y10S 364/901; Y10S 436/901
USPC ....................................................... 436/96, 91
See application file for complete search history.

(56) References Cited

FOREIGN PATENT DOCUMENTS

WO    WO 93/09431 A1    5/1993
WO    WO 93/20438 A1    10/1993

OTHER PUBLICATIONS

Dessouky Y.M. et al., "Determination of nicotinic acid and nicotinic acid derivatives with cyanogens bromide and 1-phenyl-3-methyl-5-pyrazolone", *Journal De Pharmacie De Belgique*, Jan.-Feb. 1974:29(1):43-50.
International Search Report and Written Opinion Corresponding to International Application No. PCT/GB2011/000734; Date of Mailing: Aug. 19, 2011; 11 Pages.
Liu J. et al., "Determination of nicotine by reagent-injection flow injection photometric method", *Talanta*, vol. 47, Issue 4, Sep. 28, 1998, 833-840.
Phillipou G. et al., "Assessment of a Simple Colorimetric Procedure to Determine Smoking Status in Diabetic Subjects", *Clinical Chemistry*, vol. 40, No. 7, Jul. 1994, 1296-1298.

*Primary Examiner* — Christine T Mui
(74) *Attorney, Agent, or Firm* — Myers Bigel Sibley & Sajovec, P.A.

(57) ABSTRACT

The present invention relates to assays for detection of nicotine metabolites, in particular cotinine, in fluid samples and uses of these assays in quantification of smoking habits. The assays comprise contacting a body fluid sample with a cyanogen halide and a pyrazolone compound and detecting a change in light absorbance of the pyrazolone compound which is associated with the presence of nicotine metabolites. Also provided are assay kits including a cyanogen halide or cyanogen halide-precursor(s) and a pyrazolone compound.

8 Claims, 11 Drawing Sheets

DETECTION OF NICOTINE METABOLITES

RELATED APPLICATIONS

This application is a 35 U.S.C. §371 national phase application of PCT Application PCT/GB2011/000734, filed May 13, 2011, which claims priority to GB 1008039.8, filed May 13, 2010. The entire content of each of these applications is incorporated herein by reference.

TECHNICAL FIELD

The present disclosure relates to assays for detection of nicotine metabolites, in particular cotinine, in fluid samples and uses of these assays in quantification of smoking habits.

BACKGROUND

The determination of cotinine in serum, urine and saliva is widely used as a quantitative marker of cigarette smoking/smoke intake, on account of its sensitivity and specificity [Pojer et al., Clinical Chemistry, 1984, 30, 1377-1380], particularly for research on smoking-related diseases [Hill et al., Journal of Chronic Diseases, 1983, 36, 439-449], and health risks associated with passive smoking [Jarvis et al., Thorax, 1983, 38, 829-833]. Cotinine is more sensitive than nicotine since it has a longer plasma half-life, in the region of ~11-37 hours, compared with ~30 minutes for nicotine.

Cotinine level monitoring can be used to provide an objective quantitative assessment of smoking status, which is a useful addition to self-reported smoking information (such as number of cigarettes smoked per day), which can be unreliable, partly due to differences in inhalation as a result of individual smoking techniques [Vogt et al., Preventive Medicine, 1979, 8, 23-33; Pettiti et al., American Journal of Public Health, 1981, 71, 308-311; Hall et al., Clinical Phamacology & Therapeutics, 1984, 35, 810-814; Lewis et al., Biomarkers, 2003, 8, 218-228; Britton et al., Journal of Obstetric, Gynecologic, & Neonatal Nursing, 2004, 33, 306-311; Studts et al., Cancer Epidemiology Biomarkers & Prevention, 2006, 15, 1825-1828; Gorber et al., Nicotine & Tobacco Research, 2009, 11, 12-24]. Cotinine is often referred to as the major nicotine metabolite, however some investigations have shown it to account for only ~2-30% of total nicotine metabolites in urine, and total colorimetric assay of numerous nicotine breakdown products to give equivalent cotinine values ~8 times higher than radioimmunoassay (RIA) of cotinine only levels in the same samples [Barlow et al., Clinica Chimica Acta, 1987, 165, 45-52]. Thus cotinine, although being a significant nicotine metabolite, is just one of many metabolites in the metabolic degradation sequence of nicotine (FIG. 1), and nicotine metabolite ratios can be used for prediction of cigarette consumption [Benowitz et al., Nicotine & Tobacco Research, 2003, 5, 621-624].

Methods for cotinine analysis include colorimetric methods, gas chromatography (GC) and gas chromatography-mass spectrometry (GC-MS), high-performance liquid chromatography, and radioimmunoassay (RIA). The GC and HPLC methods are not suited to either large-scale studies (such as epidemiological studies) or routine assessment of smoking status since the equipment is expensive, requires skilled staff for reliable reproducible operation and the methods are time consuming. The RIA methods are more amenable to general use but the reagents are not widely available.

Colorimetric methods are initially based upon a chemical reaction similar to that originally described by König [Journal für Praktische Chemie, 1904, 70, 19-56 & Journal für Praktische Chemie, 1904, 69, 105-137]. An example of the chemistry used in such an assay is shown in FIG. 2 using Meldrum's acid as an example.

These colorimetric methods may be used as stand-alone assays or as pre- or post-column derivatisation methods for HPLC. Chromophore-generating reagents may include barbituric acid (BA), 1,3-diethyl-2-thiobarbituric acid (DETBA), and Meldrum's acid (MA).

Cotinine equivalent measurements may use cyanide and a chromophore-generating reagent (e.g. BA, MA, DETBA) for determination of pyridine derivatives (specifically nicotine metabolites). BA is known for use with some pyridine derivatives for such colorimetric determinations of cyanide. DETBA and MA have been incorporated into near-patient/point-of-care (poc) tests for nicotine metabolites in urine or saliva to assess smoking habit [Cope et al., Annals of Clinical Biochemistry, 2000, 37, 666-673], provide biochemical feedback to improve smoking cessation interventions [Cope, Smoking Cessation: Theory, Interventions and Prevention (Landow, J. E. (ed.)), Nova Science Publishers, Inc., New York, N.Y., USA, 2008, pp. 373-383], and quantify exposure to environmental tobacco smoke [Cope et al., Annals of Clinical Biochemistry, 2000, 37, 795-796].

We now provide an improved colorimetric nicotine-metabolite (such as cotinine) assay using a pyrazolone as chromophore-generating agent. Also provided is a method of detecting and/or quantitatively measuring nicotine-metabolite concentration (such as cotinine concentration) in sample (such as a human body fluid sample) and methods which relate this concentration to smoking habit. Nicotine-metabolite assay kits also form part of the present disclosure as are near-patient/point-of-care (poc) tests for assessment of smoking habit.

SUMMARY

In one aspect the present application provides a method of detecting or measuring a nicotine metabolite in a sample comprising contacting the sample with a cyanogen halide and a pyrazolone compound and detecting a spectroscopic change, such as a change in light absorbance, of the pyrazolone compound.

This application also relates to a kit for detection or measurement of a nicotine metabolite in a sample, the kit comprising a cyanogen halide or cyanogen halide-precursor and a pyrazolone compound. In preferred aspects, this kit may further comprise a reference against which the colour of the sample may be compared.

DETAILED DESCRIPTION

Figure 1:
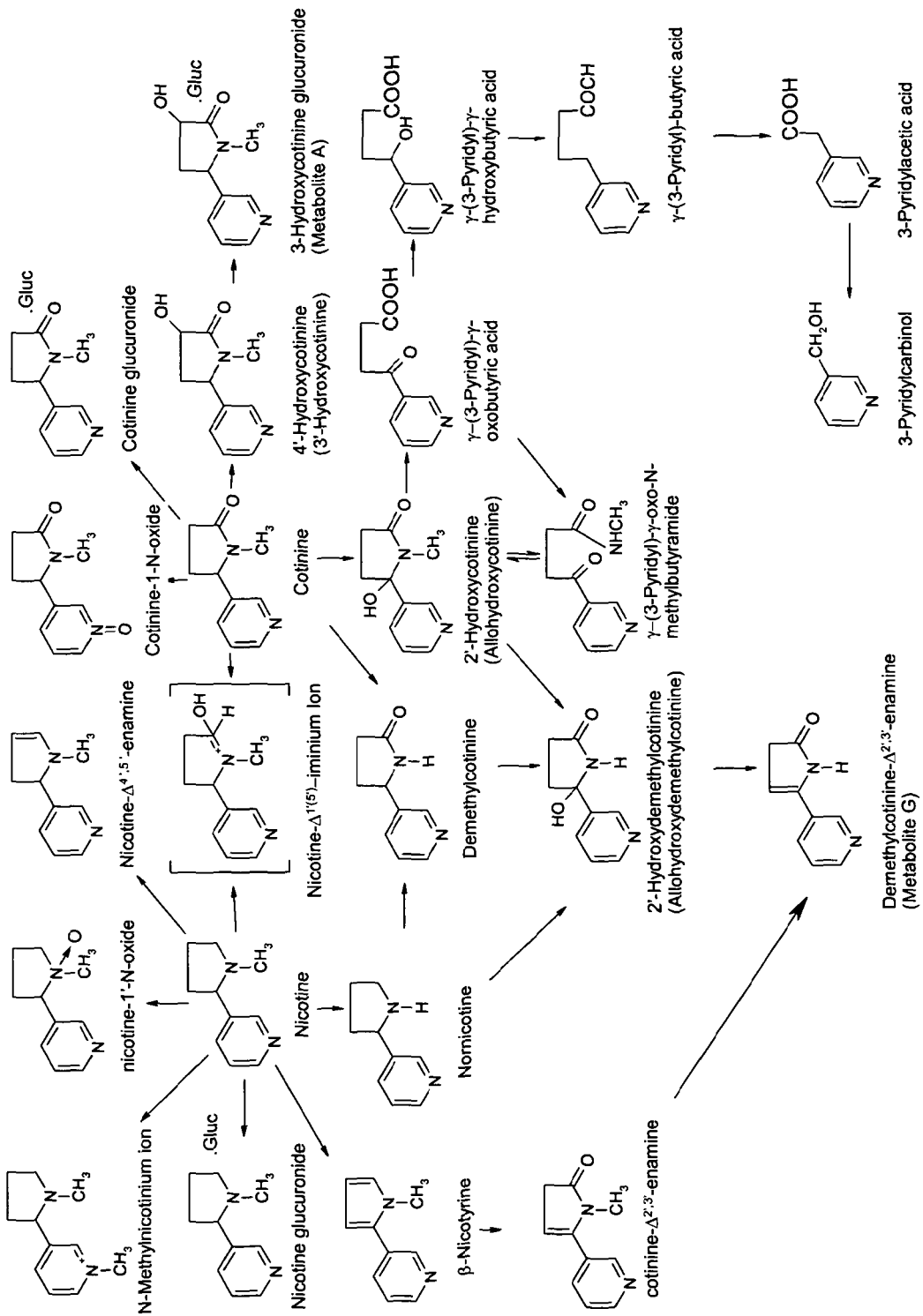
FIG. 1 shows nicotine metabolic pathways—reproduced from McKennis, H., Journal of Biological Chemistry, 1964, 239, 3990-3996 and Proceedings of the Society for Experimental Biology & Medicine, 1961, 107, 145-148, and Kyerematen, G. A., and Vesell, E. S., Drug Metabolism Reviews, 1991, 23, 3-41
Figure 2:
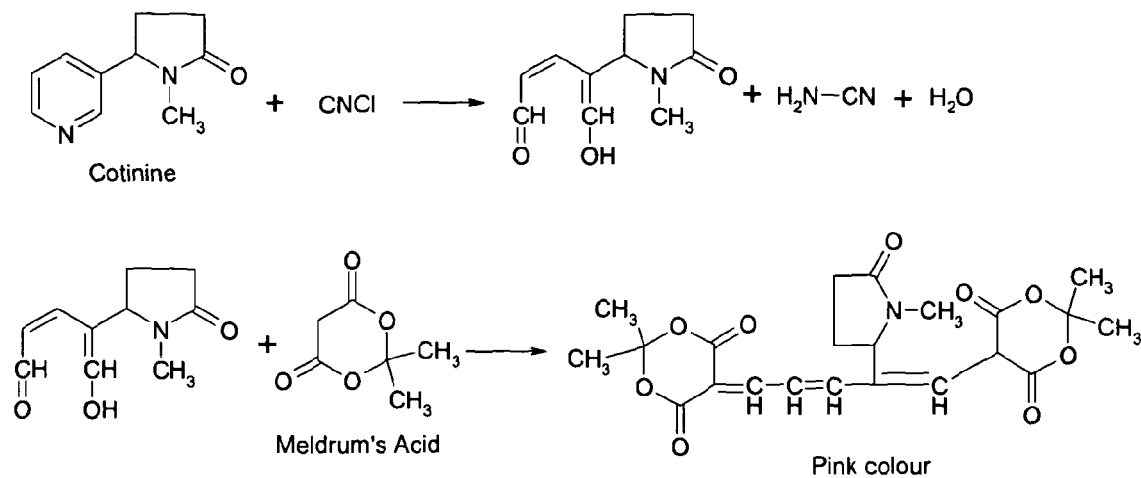
FIG. 2. Spectrophotometric assay chemistry (using Meldrum's acid for example).

The pyrazolones useful in the aspects of the present application may be compounds according to formula I

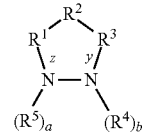

Formula I

In which:
one of $R^1$, $R^2$ and $R^3$ is —C(=O)—;
one of $R^1$, $R^2$ and $R^3$ is —CH$_2$—;
one of $R^1$, $R^2$ and $R^3$ is —C($R^6$)($R^7$)— or —C($R^6$)=;
$R^4$, $R^5$, $R^6$ and $R^7$ are each independently selected from: $C_{3-10}$ aryl, $C_{3-10}$ heteroaryl, $C_{1-6}$ alkyl, $C_{1-6}$ heteroalkyl, $C_{3-6}$ cycloalkyl, $C_{3-6}$ heterocycloalkyl and $C_{2-6}$ alkenyl, each of which may be substituted with one or more substituents selected from R, halogen, —OH, —OR, —COOH, COOR, —N(R)H, —NRR', =O, —SH, —CN, —NO$_2$, —S(=O)R, —S(=O)$_2$R, —S(=O)OH, —S(=O)$_2$OH, —S(=O)OR and —S(=O)$_2$OR, in which R and R' are selected from H, $C_{1-6}$ alkyl, $C_{2-6}$ alkenyl and $C_{1-6}$ haloalkyl; or $R^6$ and $R^7$ are together a =O group;
z and y are each independently a single or double bond;
a and b are independently 0 or 1; with the provisos that:
when $R^1$ is —C($R^6$)—, z is a double bond and a is 0, otherwise z is a single bond and a is 1; and
when $R^3$ is —C($R^6$)—, y is a double bond and b is 0, otherwise y is a single bond and b is 1.

Preferably $R^4$ and $R^5$ are independently selected from $C_{3-10}$ aryl and $C_{3-10}$ heteroaryl, more preferably $C_{3-10}$ aryl, more preferably $C_{5-7}$ aryl, more preferably phenyl each of which may be substituted as mentioned above.

If the $R^4$ or $R^5$ group is substituted, the substituent group is preferably selected from R, halogen, —OH, —OR, —COOH, COOR, —N(R)H, —NRR', =O, —SH, —CN, —NO$_2$, —S(=O)R, —S(=O)$_2$R, —S(=O)OH, —S(=O)$_2$OH, —S(=O)OR and —S(=O)$_2$OR, in which R and R' are selected from H, $C_{1-6}$ alkyl, $C_{2-6}$ alkenyl and $C_{1-6}$ haloalkyl; more preferably the substituent is selected from —S(=O)R, —S(=O)$_2$R, —S(=O)OH, —S(=O)$_2$OH, —S(=O)OR and —S(=O)$_2$OR; more preferably —S(=O)OH and —S(=O)$_2$OH; most preferably —S(=O)$_2$OH.

In some preferred embodiments $R^4$ and $R^5$ are unsubstituted.

In most preferred embodiments, $R^4$ and $R^5$ are selected from phenyl and sulfophenyl (i.e. -Ph-S(=O)$_2$OH), in particular 4-sulfophenyl.

Preferably:
one of $R^1$, $R^2$ and $R^3$ is —C(=O)—;
one of $R^1$, $R^2$ and $R^3$ is —CH$_2$—; and
one of $R^1$, $R^2$ and $R^3$ is —C($R^6$)—.
More preferably:
one of $R^1$ and $R^3$ is —C(=O)— and the other is —C($R^6$)—; and
$R^2$ is —CH$_2$—.

$R^6$ and $R^7$ are preferably independently selected from $C_{1-6}$ alkyl, $C_{1-6}$ heteroalkyl and $C_{2-6}$ alkenyl; preferably $C_{1-6}$ alkyl (such as methyl, ethyl, propyl, i-propyl, butyl, n-butyl, t-butyl, i-butyl, sec-butyl, pentyl, i-pentyl, n-pentyl, hexyl, and n-hexyl); preferably methyl; each of which may be substituted as mentioned above.

Where $R^6$ or $R^7$ are substituted, the substituent group may be selected from R, halogen, —OH, —OR, —COOH, COOR, —N(R)H, —NRR', =O, —SH, —CN, —NO$_2$, —S(=O)R, —S(=O)$_2$R, —S(=O)OH, —S(=O)$_2$OH, —S(=O)OR and —S(=O)$_2$OR, in which R and R' are selected from H, $C_{1-6}$ alkyl, $C_{2-6}$ alkenyl and $C_{1-6}$ haloalkyl; preferably —OH, —OR, —COOH, COOR, —N(R)H, —NRR', =O, —SH, —CN, —NO$_2$.

More preferably $R^6$ and $R^7$ are unsubstituted.

In some preferred embodiments,
$R^1$ is —C(=O)—;
$R^2$ is —CH$_2$—;
$R^3$ is —C($R^6$)—; and
$R^5$ is $C_{3-10}$ aryl (preferably phenyl) optionally substituted with —S(=O)OH or —S(=O)$_2$OH (preferably —S(=O)$_2$OH).

Some preferred embodiments of the compounds of formula I include compounds of formulae II, III or IV.

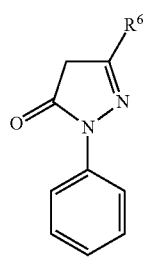

II

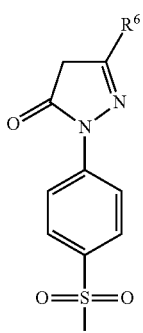

III

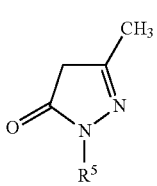

IV

Wherein $R^5$ and $R^6$ are as defined for formula I.

The options and preferences mentioned herein for one part of the compounds may be freely combined in a single embodiment with options and preferences mentioned separately for other parts of the compounds.

Particularly preferred compounds according to formula I are 3-methyl-1-phenyl-2-pyrazoline-5-one (MPP) and 1-(4-sulfophenyl)-3-methyl-2-pyrazolone (SPMP).

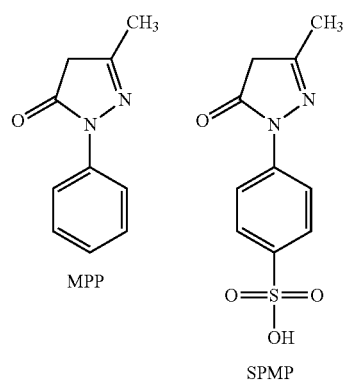

MPP                    SPMP

The pyrazolone compounds according to formula I are useful in the present assays because they exhibit a change in light absorbance on reaction with a dialdehyde component (which can be easily obtained in the present assay from nicotine metabolites). Particularly preferred pyrazolone compounds are those which exhibit changes in light absorbance in the visible light region of the spectrum, so allowing a visual assessment of the outcome of the assay.

The assay methods described herein may be sensitive to a range of nicotine metabolites, in particular those containing a pyridine ring. Examples of nicotine metabolites that maybe detected by these assays include N-methylnicotinium ion, nicotine-1'-N-oxide, nicotine-$\Delta^{4',5'}$-enamine, nicotine glucuronide, nicotine-$\Delta^{1'(5')}$-iminium ion, β-nicotyrine, nornicotine, demethylcotinine, cotinine-$\Delta^{2',3'}$-enamine, allohydroxydemethylcotinine, demethylcotinine-$\Delta^{2',3'}$-enamine, cotinine, cotinine-1-N-oxide, cotinine glucuronide, 3'-hydroxycotinine, allohydroxycotinine, γ-(3-pyridyl)-γ-oxo-N-methylbutyramide, γ-(3-pyridyl)-γ-oxobutyric acid, 3-hydroxycotinine glucuronide, γ-(3-pyridyl)-γ-hydroxybutyric acid, γ-(3-pyridyl)-butyric acid, 3-pyridylacetic acid and 3-pyridylcarbinol.

Preferably, the assay methods are sensitive at least to cotinine.

Biological samples will tend to contain a number of different pyridine ring-containing nicotine metabolites (as detailed previously, and shown in FIG. 1), which may produce a range of slightly different chromophores in the assay (when using any of the chromophore-generating reagents). These chromophores may all have slightly different lmax wavelengths and response factors. Therefore measurement at a single wavelength and calibration with a single standard (cotinine) provides a value for total nicotine metabolites. However, this tends to be better than techniques that specifically detect cotinine only since they are more susceptible to fluctuations due to smoking frequency and individual metabolism with respect to nicotine breakdown.

In the assay methods described herein, the sample is contacted with a cyanogen halide which reacts with the nicotine metabolite (specifically with the pyridine ring in the nicotine metabolite) to form an N-cyanopyridinium ion which, on hydration, eliminates cyanamide and opens the pyridine ring to form a dialdehyde.

The cyanogen halide used may be selected from cyanogen fluoride, cyanogen chloride, cyanogen bromide and cyanogen iodide and is preferably cyanogen chloride.

Cyanogen chloride is gaseous (at room temperature and pressure) so it may be advantageous to produce it in-situ by known methods such as by reaction of cyanide ions (e.g. from KCN, NaCN or KSCN) with a source of electrophilic chlorine, such as chloramine-T (N-chloro tosylamide sodium salt), or by reaction with chlorine gas.

Preferably cyanogen chloride is produced in-situ in the assay by reaction of KCN with chloramine-T, preferably in a ratio of about 1:1 w/w. This is advantageous because both compounds are solids at room temperature and pressure so handling and storage are relatively easy.

When the pyridine ring has been opened by reaction with cyanogen halide to form a dialdehyde, the dialdehyde reacts with the pyrazolone compound (more specifically with a —$CH_2$— group on the pyrazolone) to form a conjugate which has a different light absorbance profile to the unconjugated components.

In preferred embodiments, the sample is first contacted with the cyanogen halide (which may have been generated in-situ) and is subsequently contacted with the pyrazolone compound.

The change in light absorbance which occurs on conjugation of the dialdehyde (derived from the nicotine metabolite) and the pyrazolone compound may be a change in absorbance of any wavelength of light but is preferably a change in the absorbance in the visible light range, more preferably a change in the colour of the assay mixture. This has the advantage that the detection of nicotine metabolite can be visually determined. When the most preferred MPP and SPMP pyrazolones are used, the assay mixture generates a pink colour in the presence of nicotine metabolites such as in the presence of cotinine. Of course, the original sample may itself be slightly coloured (e.g. slightly yellow for urine) but in preferred embodiments, the pink colour generated by the assay mixture is more intense than the colour of the original sample (i.e. the absorbance in the pink region of the spectrum is stronger than that in the region corresponding to the original colour of the sample).

Figure 4:
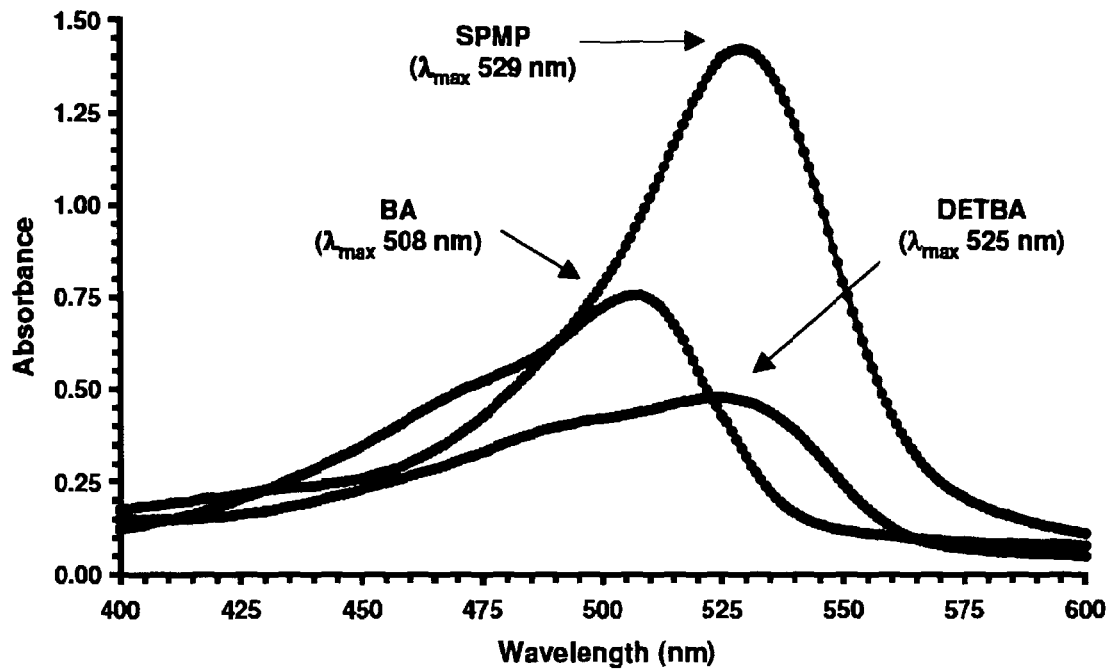
FIG. 4. shows spectrophotometric assay 'wavescans' for selected chromophore-generating reagents (5 µg/mL cotinine standard): (a) SPMP (~15 minutes incubation, lmax=529 nm); (b) BA (~10 minutes incubation, lmax=508 nm); (c) DETBA (~20 minutes incubation, lmax=525 nm) (averaged results of triplicate analyses).
Figure 5:
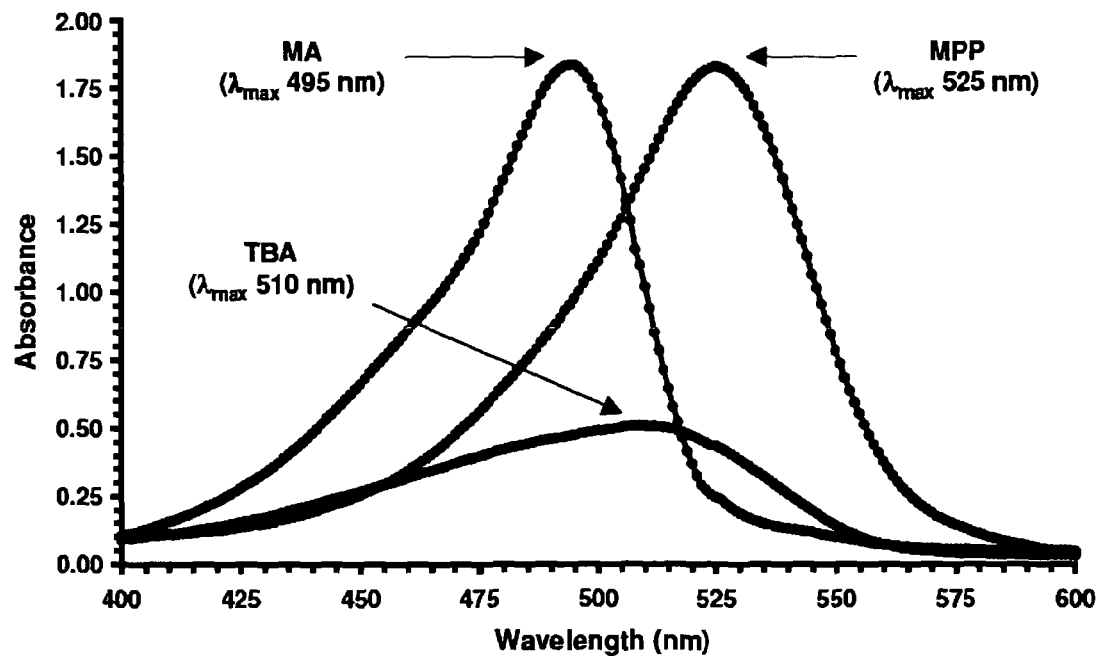
FIG. 5. shows spectrophotometric assay 'wavescans' for selected chromophore-generating reagents (10 μg/mL cotinine standard): (a) MA (~25 minutes incubation, lmax=495 nm); (b) MPP (~10 minutes incubation, lmax=525 nm); (c) TBA (~20 minutes incubation, lmax=510 nm) (averaged results of triplicate analyses).

Absorption spectra are shown in FIGS. 4 and 5 for assay reaction mixtures using a variety of different chromophore-generating compounds, including the preferred MPP and SPMP, in contact with a standard cotinine sample. It can be seen that both MPP and SPMP exhibit intense absorption peaks indicating a strong colour change on introduction of the nicotine metabolite to the assay mixture.

The assay may be performed in any suitable solvent. Aqueous solvents are preferred and an acetone/water mixture is most preferred.

The reaction mixture may also contain buffers to control solution pH. In preferred embodiments an acetate buffer (e.g. sodium acetate/acetic acid) or citrate (sodium citrate/citric acid) is added to the reaction mixture to buffer the pH to a pH in the range 4.5 to 4.9, preferably pH 4.7. Above pH 4.9 and below pH 4.5, the response of the assay may be impaired.

In preferred embodiments of the present methods, the level of absorbance of the pyrazolone-dialdehyde conjugate varies quantitatively with the amount of nicotine metabolite present in the sample. Typically the wavelength of the absorbance maximum remains the same and the intensity of the absorbance varies with concentration of the nicotine metabolite.

In some embodiments, this level of absorbance may be measured spectroscopically or, in some embodiments, it may be possible to make a visual determination of the absorbance level by comparison against a reference. For example it may be possible to determine the absorbance level (and hence the concentration of nicotine metabolite in the sample) by visual comparison of the colour of the reaction mixture with reference colours (provided, for example, on a colour chart or as reference solutions).

It is known that nicotine metabolite levels in body fluid samples may be correlated to smoking habits. Therefore in some preferred embodiments it may be possible to infer smoking habits by visual assessment of the colour of a reaction mixture defined herein.

Figure 14:
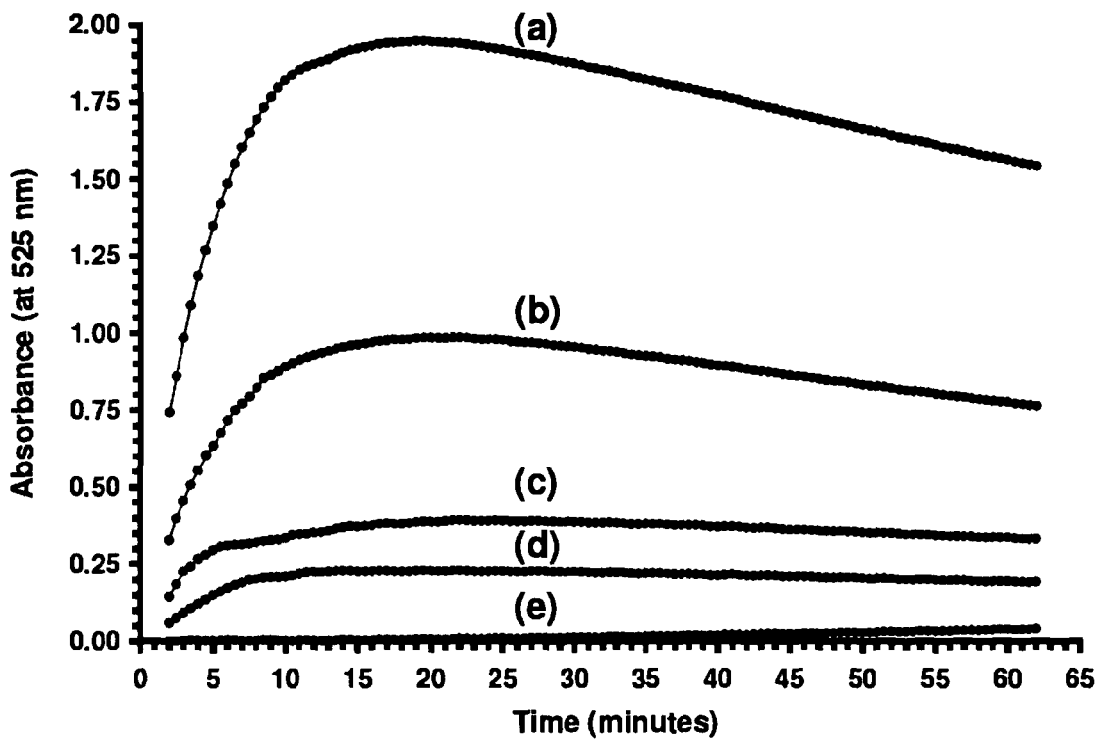
FIG. 14. Spectrophotometric assay 'timedrives' for cotinine standards ((a) 10 μg/mL; (b) 5 μg/mL; (c) 2 μg/mL; (d) 1 μg/mL; (e) 0 μg/mL (blank)) using 3-methyl-1-phenyl-2-pyrazoline-5-one (MPP) as the chromophore-generating reagent (absorbance at 525 nm) (averaged results of triplicate analyses).
Figure 16:
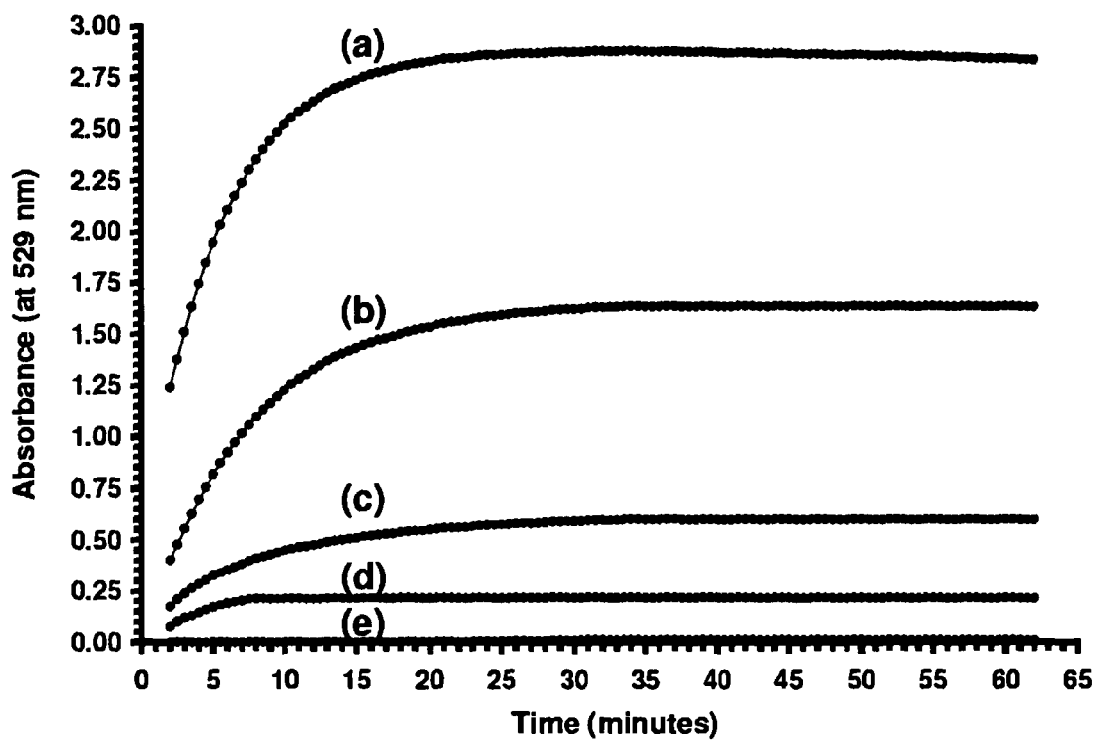
FIG. 16. Spectrophotometric assay 'timedrives' for cotinine standards ((a) 10 μg/mL; (b) 5 μg/mL; (c) 2 μg/mL; (d) 1 μg/mL; (e) 0 μg/mL (blank)) using 1-(4-sulfophenyl)-3-methyl-5-pyrazolone (SPMP) as the chromophore-generating reagent (absorbance at 529 nm) (averaged results of triplicate analyses).

In some embodiments of the present methods, it may be preferred to allow the reaction mixture to develop the change in light absorbance for a period of time before the absorbance measurements are made. Preferably the reaction mixture is allowed to develop for at least about 5 minutes and preferably less than about 60 minutes, more preferably between about 10 minutes and about 40 minutes, most preferably between about 10 minutes and about 20 minutes, before the absorbance measurements are made. If the reaction mixture is allowed to develop for less than about 5 minutes, the level of absorbance may not have reached its optimum (preferably maximum) value at which it provides a quantitative relationship with the amount of nicotine metabolite in the sample. On the other hand, if the reaction mixture is allowed to develop for more than about 60 minutes the level of absorbance may start to fall, as the conjugate which provides the change in absorbance degrades, so a measurement of the absorbance level may not provide a quantitative measure of the amount of nicotine metabolite present in the sample. FIGS. 14 and 16 show examples of the variation of absorbance intensity over time for MPP and SPMP respectively.

Nicotine metabolites may be present in a variety of different biological samples following nicotine ingestion and especially in bodily fluids. Therefore the present methods are useful to detect nicotine metabolites in biological samples, such as bodily fluids, e.g. saliva, urine, whole blood or blood products, sweat, semen, amniotic fluid or meconium. In preferred embodiments of the present methods, nicotine metabolites are detected in saliva samples.

Therefore, the present disclosure provides a method for detecting (preferably quantitatively) nicotine metabolites in a body fluid sample. This can be used as a sensitive measure of smoking habits, such as how many cigarettes are smoked in a day due to the longer half-life of nicotine metabolites (especially cotinine) in the human body when compared to the lifetime of nicotine itself. The present methods can be used to quantitatively detect smoking levels as low as 1 to 2 cigarettes per day and the results from these methods are shown to correlate well with self-reported smoking levels.

The present methods can also be used to monitor levels of nicotine being administered to a subject as nicotine replacement therapy. The present methods provide an accurate monitor of the exact levels of nicotine absorbed by the subject so allowing careful and individualised adjustment of the levels of nicotine administered in the replacement therapy. Therefore, the present disclosure also provides a method of optimising a nicotine replacement therapy comprising administering a known dosage level of nicotine to a subject; measuring the level of one or more nicotine metabolites in a body fluid sample from the subject; and adjusting the administered nicotine dosage level based on the level of nicotine metabolites in the body fluid sample to optimise the level of nicotine absorbed by the subject, e.g. to adjust the amount of nicotine administered to result in the absorption of a known desired amount of nicotine, e.g. in the bloodstream of the subject.

The sensitivity of the present methods is shown to be superior to known nicotine metabolite detection. In comparisons with other chromophore generating agents (agents which react with the dialdehyde component of the reaction to provide a change in light absorbance), the preferred SPMP and MPP outperformed Meldrum's acid (MA), Barbituric acid (BA), 1,3-diethyl-2-thiobarbituric acid (DETBA) and 2-thiobarbituric acid (TBA). The order of sensitivity of assays using each of these chromophore generating agents is SPMP>MPP≈MA>BA>DETBA≥TBA.

In some embodiments (as shown in the examples), SPMP is shown to have a response factor of about 2.8-2.9 when normalised against 1.0 for DETBA and about 1.4-1.5 when normalised against MA. In other embodiments (shown in the examples) MPP is shown to have a response factor of about 1.9 when normalised against 1.0 for DETBA and about 1.0 when normalised against MA.

Preferably the quantitative visual lower detection limit for cotinine in the present assays is about 0.8 µg/mL or less, more preferably about 0.5 µg/mL or less and even more preferably about 0.3 µg/mL or less. The spectroscopic lower detection limit is preferably about 0.7 µg/mL or less, more preferably about 0.3 µg/mL or less and even more preferably about 0.2 µg/mL or less.

The sensitivity of the present methods and compositions is high enough to enable detection of passive smoking in a subject, for example passive smoking in infants and children. [For the detection of passive smoking, the levels of the nicotine metabolites in saliva samples are likely to be very low so it is preferable to use a urine sample for passive smoking detection]. Therefore, it is also an aspect of the present invention to provide a method for detection of passive smoking, preferably passive smoking in children, by contacting a body fluid sample (preferably a urine sample) with a composition as described herein, and detecting any change in the level of light absorbance of the pyrazolone component of the composition.

In addition to the improved sensitivity, SPMP and MPP also have the advantage that the change in absorbance on detection of nicotine metabolites corresponds to a colour change from colourless to pink. This is preferable to the change exhibited by, for example, MA which is from colourless to pale yellow which is a difficult change to detect visually (so limiting the sensitivity of the assay at low nicotine metabolite levels) and the range of colour intensity produced by reaction with different concentrations of nicotine metabolites is relatively narrow so visual assessment of the differences associated with different concentrations of nicotine metabolites is difficult. However, the pink colour of SPMP and MPP is more intense so is easier to detect visually in low amounts (corresponding to low nicotine metabolite concentrations) but also has a relatively wider range of colour intensity associated with different nicotine metabolite concentrations so a visual quantitative analysis of the concentration is easier due to the relatively larger variation in colour intensity with a given change in nicotine metabolite concentration.

The present proposals also include a kit for detection or measurement of a nicotine metabolite in a sample. Such a kit includes at least a cyanogen halide (or cyanogen halide precursors) and pyrazolone compound as defined above. In preferred embodiments these compounds are contained in a closed reaction vessel which includes a wall region through which a sample to be tested can be introduced, preferably in a sealable manner so that the compounds and sample inside the reaction vessel are substantially isolated from the outside environment. This is preferred because the cyanogen halide is toxic and the contents of the vessel after reaction may present a biohazard (due to use of biological samples) so it is important to minimise the user's exposure to the reagents inside the vessel. Any known way of achieving this isolation of the reaction components from the user may be employed, such as SafeTube™ technology [described in WO 93/09431].

Preferably the assay kit also comprises reference material which relates the colour of the reaction mixture to the concentration of nicotine metabolite(s) in the sample so allowing a visual assessment of the concentration in the sample without requiring laboratory analysis. Examples of such reference materials are known, such as printed material (e.g. a colour chart) showing the different colours of the reaction mixture which correlate with different concentrations of nicotine metabolite in the sample or a range of coloured samples (e.g. liquid samples) the colours of which correlate with different concentrations of nicotine metabolite in the sample.

Preferably, the kit comprises the reagents KCN, chloramine-T and SPMP in a KCN:chloramine-T:SPMP ratio of about 1:1:0.2 w/w.

The kit described in the present proposals provides a simple point-of-care (poc) test for the assessment of smoking habit. Such a poc test could be useful, for example, to measure patient compliance/progress in smoking cessation programmes, to ensure an accurate assessment of smoking habits (e.g. for the medical or health insurance industry) etc.

EXAMPLES

The following examples are provided to illustrate specific embodiments of the invention. They do not limit the scope of the claims and a skilled person will be able to envisage alternative ways of putting the invention into effect within the scope of the claims.

Reagents

Suitable analytical-reagent grade chemicals were utilised as indicated throughout, and all were obtained from Sigma-Aldrich Ltd (Gillingham, UK). Unless otherwise stated, tap water purified by filtration, ion exchange, reverse osmosis, and UV treatment using an Elga Option 3 water purifier (Elga Process Water UK, Marlow, UK), referred to hereafter as 'deionised water', was utilised throughout for solution preparation.

A stock (−)-cotinine standard solution (100±0.5 µg/mL) was prepared by dissolving 100±0.5 mg of cotinine in deionised water (1 L). Aliquots of this solution (~10 mL each) were frozen (−20° C.), and gently thawed and mixed under ambient conditions immediately before use, as required. Appropriate dilution of such aliquots with deionised water (or centrifuged non-smoker's saliva, NSS) was performed to produce a range of cotinine standard solutions (0-10 µg/mL) for spectrophotometric assay calibration (as detailed below).

The following chromophore-generating reagent solutions were prepared:
barbituric acid (BA, 1% w/v);
1,3-diethyl-2-thiobarbituric acid (DETBA, 1% w/v in acetone/water (1:1 v/v));
Meldrum's acid (MA, 2,2-dimethyl-1,3-dioxane-4,6-dione, 1% w/v in acetone/water (1:1 v/v));
2-thiobarbituric acid (TBA, 1% w/v);
1,3-indandione (0.4% w/v);
1,3-cyclohexanedione (0.4% w/v);
5,5-dimethyl-1,3-cyclohexanedione (0.4% w/v);
4-cyclopentene-1,3-dione (0.4% w/v);

4-hydroxy-5-methyl-4-cyclopentene-1,3-dione monohydrate (0.4% w/v);
3-methyl-1-phenyl-2-pyrazoline-5-one (MPP, 0.4% w/v);
and 1-(4-sulfophenyl)-3-methyl-5-pyrazolone (SPMP, 0.4% w/v).

Figure 3:
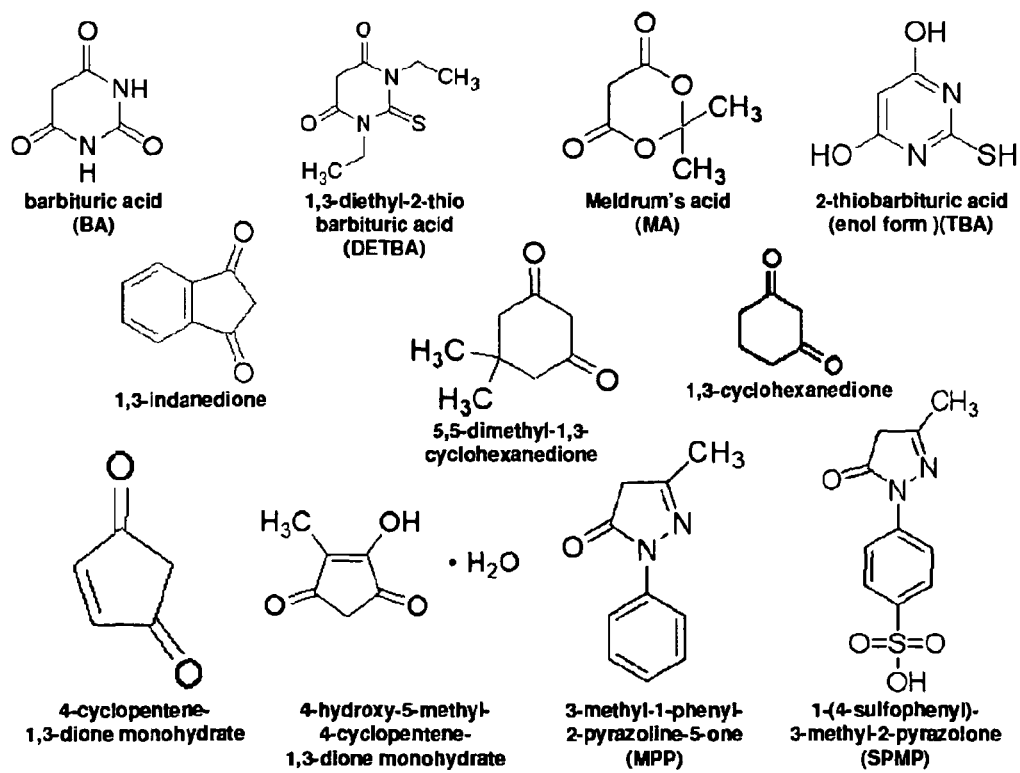
FIG. 3. Known and potential assay chromophore-generating reagents.

The chemical structures of these compounds are shown in FIG. 3.

A range of acetate buffers (4 M, pH 3.7-5.7 at 0.2±0.01 intervals) were prepared by mixing appropriate quantities of sodium acetate (4 M) and acetic acid (4 M) solutions.

All solutions were filtered using Klarity® nylon filters (13 mm, 0.22 µm, Qmx Laboratories, Thaxted, UK), to reduce risk of particulate-interference during spectrophotometric measurement.

All reagents were stored in a refrigerator (4° C.) when not in use. Chloramine-T solution was freshly prepared on a daily basis as required. All other solutions were stable for at least 1 week when stored in a refrigerator (4° C.)

Instruments and Software

Reagents were weighed out using a Mettler-Toledo AT261 DeltaRange® analytical balance (Mettler-Toledo Ltd, Leicester, UK).

pH measurements were performed using an EDT Instruments GP353 ATC pH meter (EDT Instruments Ltd, Dover, UK), calibrated daily using freshly prepared pH 4.0, 7.0 and 10.0 calibration solutions.

Centrifugation was performed using a Jouan MR1822 centrifuge (Jouan, Newport Pagnell, UK), as detailed below.

A Pharmacia Ultrospec 4000 UV/Visible Spectrophotometer (Amersham Pharmacia Biotech UK Ltd, Little Chalfont, UK) equipped with an 8-way cell changer and glass cuvettes (0.7 mL, 1 cm path length), controlled by pc using Swift II software (v. 1.01), was utilised throughout for collection of all absorbance measurement data (as detailed below). 'Timedrive' and 'wavescan' curves generated using Swift II software were manipulated using Microsoft Excel™.

Saliva Sample Collection and Preparation

Saliva samples were collected from volunteers by repeated expectoration into screw-cap plastic vials (20 mL) over several hours, ensuring that no food or drink was consumed for at least 30 minutes before sampling.

Saliva samples from 2 nonsmokers (NSS) were pooled (total volume~100 mL), gently mixed by manual shaking, and refrigerated (4° C.) until required.

Saliva samples from 3 smokers (SS) were collected (~10-20 mL each, labelled SS1-3) and stored separately (4° C.) until required.

Self-reported smoking levels for samples SS1-3 were <10 cigarettes/day, ~10 cigarettes/day, and ~20 cigarettes/day, respectively.

Immediately before use, saliva samples (NSS and SS) were centrifuged (10 minutes at 9000 rpm/6710 G) using a Jouan MR1822 centrifuge (Jouan, Newport Pagnell, UK). Aliquots of the supernatant from the centrifuged NSS (1350 µL) were diluted with appropriate amounts of cotinine standard solution/deionised water (total volume 150 µL) to produce a range of cotinine-spiked NSS standards for use in spectrophotometric assays (1 mL aliquots, as detailed below). Aliquots of the supernatant from the centrifuged SS (1 mL) were used directly in spectrophotometric assays (as detailed below).

Spectrophotometric Measurements

All spectrophotometric measurements ('wavescans' and 'timedrives') were performed on triplicate samples using a Pharmacia Ultrospec 4000 UV/Visible Spectrophotometer (Amersham Pharmacia Biotech UK Ltd, Little Chalfont, UK) equipped with an 8-way cell changer and glass cuvettes (0.7 mL, 1 cm path length), controlled by PC using Swift II software (v. 1.01).

'Wavescans' were performed after incubation for a specific time (as detailed) over the range 400-600 nm at a scanning speed of 2500 nm/minute, with absorbance measurements performed at 1 nm intervals.

'Timedrives' were started exactly 2 minutes after addition of chromophore generating reagent (t=0) and were performed over a period of 60 minutes; with absorbance measurements performed at 30 s intervals, at the lmax wavelength for the particular chromophore-generating reagent being used (which was determined previously by 'wavescan' absorbance measurements, as discussed below).

Absorbance measurement data generated using Swift II software for triplicate sample analyses was transferred into Microsoft Excel™ and data point values averaged accordingly. All data presented is averaged and all mean absorbance values had % variation (100×(standard deviation/mean)) values of <5% (5% error bars are therefore displayed in the Figures).

Example 1

A 0.4% (w/v) solution of 3-methyl-1-phenyl-2-pyrazoline-5-one (MPP) (structure shown in FIG. 3) in deionised water was prepared, vortex mixed (~5 minutes), and filtered (Klarity® nylon filters, 13 mm, 0.22 µm). The filtered MPP solution was used as the chromophore-generating reagent in the assay of cotinine standards (10 µg/mL).

Cotinine standard solution (0-10 µg/mL, 1 mL) was placed in a stoppered test tube (25 mL), acetate buffer (4 M, pH 4.7, 400 µL) was added, and immediate vortex mixing (~10 s) was performed using a Fisherbrand® WhirliMixer® (Thermo Fisher Scientific, Loughborough, UK). Potassium cyanide solution (10% w/v, 200 µL), chloramine-T hydrate solution (10% w/v in acetone/water (1:1 v/v), 200 µL), and chromophore generating reagent solution (1% w/v, 1 mL), were sequentially added, giving a total solution volume of 2.8 mL, followed by tube stoppering and vortex mixing (~10 s).

Timing (t=0) was commenced immediately upon addition of the chromophore generating reagent solution.

For spectrophotometric analysis, an aliquot of solution (0.7 mL) was removed by pipette from the test tube and placed in a capped glass cuvette (0.7 mL, 1 cm path length). The cuvette was placed in the cell changer of a Pharmacia Ultrospec 4000 UV/Visible spectrophotometer and subjected to 'wavescan' and 'timedrive' absorbance measurements, which commenced after a predetermined timed interval, as detailed below.

The remaining contents of the stoppered test tube (~2 mL) were retained for visual inspection during the course of the assay. On visual inspection, the solution turned a pink colour under ambient conditions after only a few minutes incubation after addition of the cotinine standard solution.

After assay completion (1 hour in the case of 'timedrives', and immediately on completion of 'wavescans'), cuvette and test tube contents were poured/washed into a container containing a freshly mixed 1:1 v/v solution of sodium carbonate solution (375 mM, 100 mL) and a solution (100 mL) containing iron (II) sulphate heptahydrate (150 mM) and citric acid (20 mM).

The wavelengths of maximum absorbance (lmax) when using MPP as the chromophore-generating reagent was determined by performing wavescans on replicate solutions generated by spectrophotometric assay of cotinine standard solutions. An example absorbance spectrum (400-600 nm) for MPP (pink colour, lmax=525 nm) for a specific cotinine concentration (10 μg/mL) and incubation time (10 minutes) is shown in FIG. 4.

Figure 15:
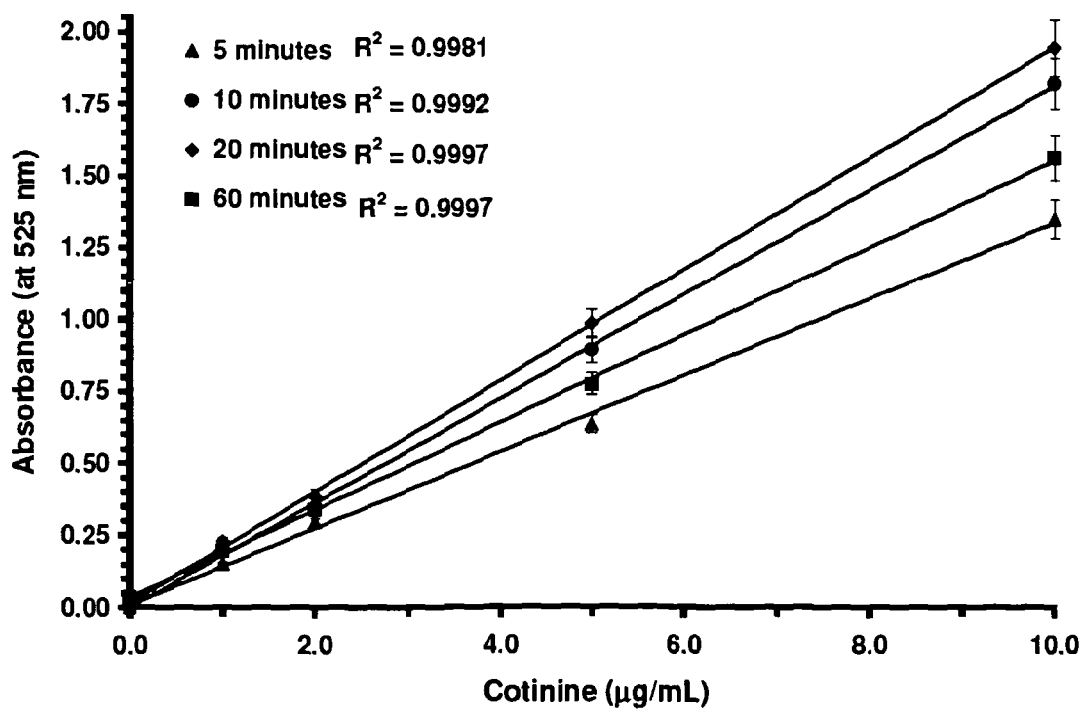
FIG. 15. Cotinine calibration curves (0-10 μg/mL) for the 3-methyl-1-phenyl-2-pyrazoline-5-one (MPP) spectrophotometric assay using absorbance data (525 nm) collected after 5, 10, 20, and 60 minutes.

A range of cotinine standard solutions (10, 5, 2, 1 and 0 (blank) μg/mL) were assayed individually in triplicate using MPP as the chromophore generating reagent, by timedrives (measuring absorbance at the reagent lmax as a function of incubation time, under ambient conditions) and averaged results are shown in FIG. 14. From these timedrives, cotinine calibration curves (concentration versus absorbance) were constructed and linear regression analysis performed for specific incubation times (5, 10, 15, 20, 25, 30, 40, 50 and 60 minutes). Selected cotinine calibration curves for spectrophotometric assays, performed in triplicate using MPP as the chromophore-generating reagent, are displayed in FIG. 15. Excellent linearity (R values >0.999) was observed for incubation times in the region 12 of 10-60 minutes (FIG. 15), with maximum absorbance occurring after ~19-22 minutes, followed by slow colour degradation, decreasing at a rate of <0.5%/minute over the next 20 minutes (FIG. 14). Single measurements can be taken at any specific time within the 10-60 minute incubation window, however for maximum colour yield and thus sensitivity the 15-30 minute window is preferred when using MPP.

The calibration curve equations determined by linear regression analysis of the absorbance versus cotinine concentration data for MPP (measured at lmax) at 5, 10, 15, 20, 25, 30, 40, 50 and 60 minutes incubation time were utilised to determine a response factor (absorbance units per mg/mL cotinine concentration unit) which is shown in Table 1.

Lower concentration cotinine standard solutions (in the range 0.2-1.0 μg/mL) were used in the assay to estimate the qualitative detection limit (limit of manual visual observance of a discernible colour compared with a reagent blank) and quantitative detection limit (limit of spectrophotometric ability to adequately distinguish between a standard and a reagent blank). This estimated detection limit value is shown in Table 1.

Example 2

Experiments were performed as in Example 1 but using 1-(4-sulfophenyl)-3-methyl-5-pyrazolone (SPMP) (structure shown in FIG. 3).

Figure 17:
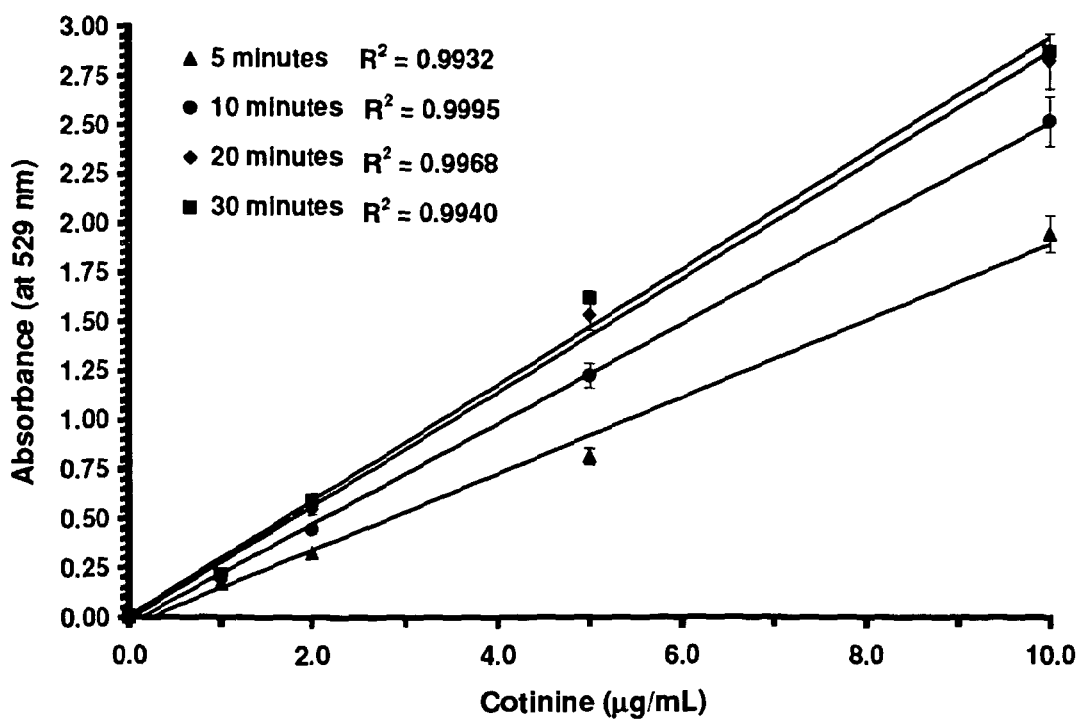
FIG. 17. Cotinine calibration curves (0-10 μg/mL) for the 1-(4-sulfophenyl)-3-methyl-5-pyrazolone (SPMP) spectrophotometric assay using absorbance data (529 nm) collected after 5, 10, 20, and 60 minutes.

Good linearity (R values >0.997) was observed for incubation times in the region of 10-40 minutes (FIG. 17), with maximum absorbance occurring after ~33-38 minutes, with no discernible degradation over the time period tested (FIG. 16). Single measurements (i.e. if not doing timedrives) should therefore preferably be taken at a specific time within the 10-40 minute incubation window when using SPMP.

The effect of pH on the response factor of SPMP in the assay was also briefly investigated to confirm that pH 4.7, was equally applicable to SPMP. Thus, analysis of a cotinine standard (5 μg/mL) using a range of acetate buffers (4 M, pH 3.7-5.7 at 0.2±0.01 intervals, prepared by mixing appropriate quantities of sodium acetate (4 M) and acetic acid (4 M) solutions), was performed. Assays performed at pH 4.5-4.9 gave essentially identical responses, however pH<4.5 and pH>4.9 resulted in reduction in response factor. Thus pH 4.7 was the pH of choice.

Example 3

Experiments were performed as in Example 2 but using non-smokers' saliva (NSS) as the solvent for the SPMP rather than deionised water. The results are shown in table 1.

Aliquots of the supernatant from the centrifuged non-smokers' saliva (NSS, 1350 μL) were diluted with appropriate amounts of cotinine standard solution/deionised water (total volume 150 μL) to produce a range of cotinine-spiked NSS standards (5, 2.5, 1.0, 0.5, 0 (diluted NSS blank) μg/mL) for triplicate analysis in the spectrophotometric assay using SPMP as the chromophore-generating reagent.

Figure 18:
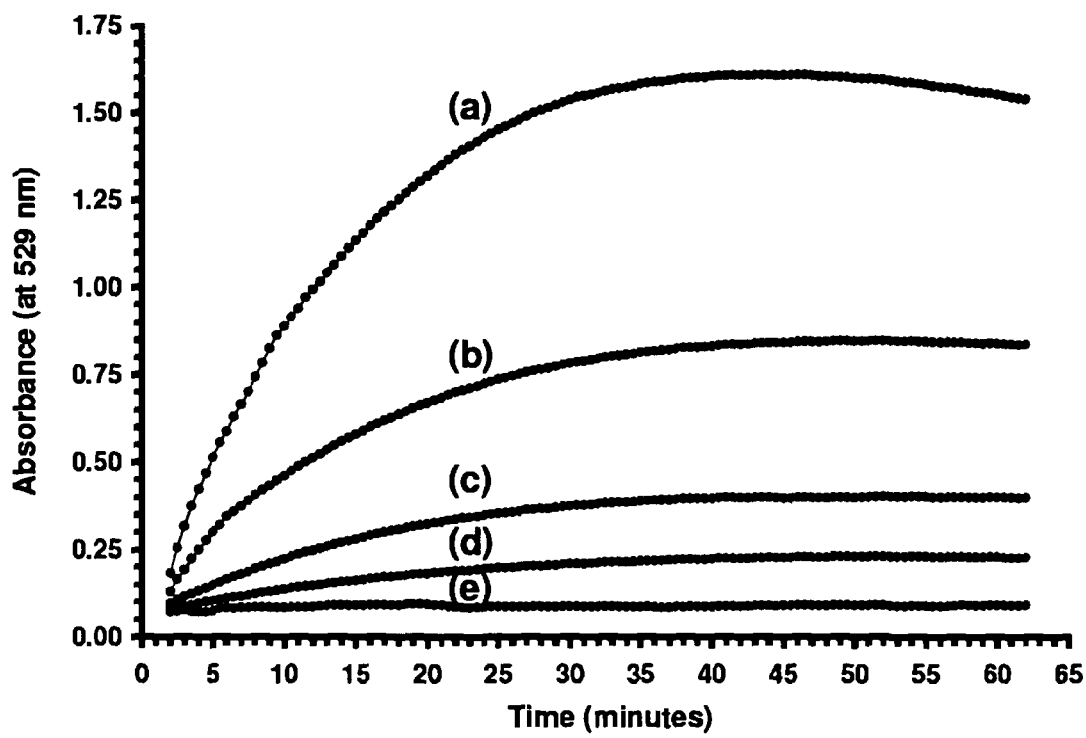
FIG. 18. Spectrophotometric assay 'timedrives' for cotinine-spiked non-smokers' saliva (NSS) standards ((a) 5.0 μg/mL; (b) 2.5 μg/mL; (c) 1.0 μg/mL; (d) 0.5 μg/mL; (e) 0 μg/mL (blank)) using 1-(4-sulfophenyl)-3-methyl-5-pyrazolone (SPMP) as the chromophore-generating reagent (absorbance at 529 nm) (averaged results of triplicate analyses).

Timedrives (measuring absorbance at the reagent lmax as a function of incubation time, under ambient conditions) were performed as shown in FIG. 18, and from this data cotinine calibration curves (concentration versus absorbance) were constructed and linear regression analysis performed for specific incubation times (5, 10, 15, 20, 25, 30, 40, 50 and 60 minutes).

Figure 19:
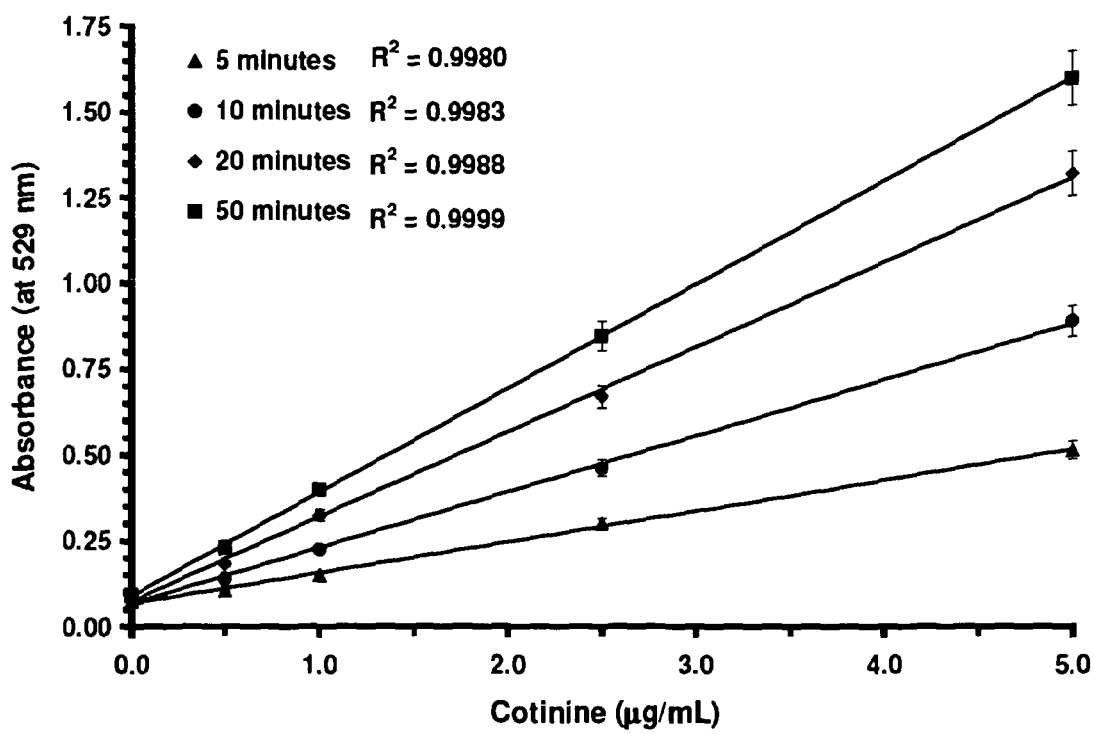
FIG. 19. Cotinine-spiked non-smokers' saliva calibration curves (0-5 μg/mL) for the 1-(4-sulfophenyl)-3-methyl-5-pyrazolone (SPMP) spectrophotometric assay using absorbance data (529 nm) collected after 5, 10, 20, and 50 minutes.

Selected cotinine-spiked NSS calibration curves for spectrophotometric assays performed in triplicate using SPMP as the chromophore-generating reagent are displayed in FIG. 19.

Excellent linearity (R values >0.999) was observed for incubation times over the entire investigated region of 10-60 minutes (FIG. 19), with maximum absorbance occurring after ~45-55 minutes, followed by very slow colour degradation, decreasing <3% over the next 10-15 minutes (FIG. 18). Single measurements can be taken at any specific time within the 10-60 minute incubation window, however for increased colour yield and thus sensitivity the 15-30 minute window is preferred.

The calibration curve equations determined by linear regression analysis of the absorbance versus cotinine concentration data for SPMP (measured at lmax) at 5, 10, 15, 20, 25, 30, 40, 50 and 60 minutes incubation time were utilised to determine the response factor (absorbance units per μg/mL cotinine concentration unit) under the employed assay conditions (Table 1).

Comparative Examples

Figure 6:
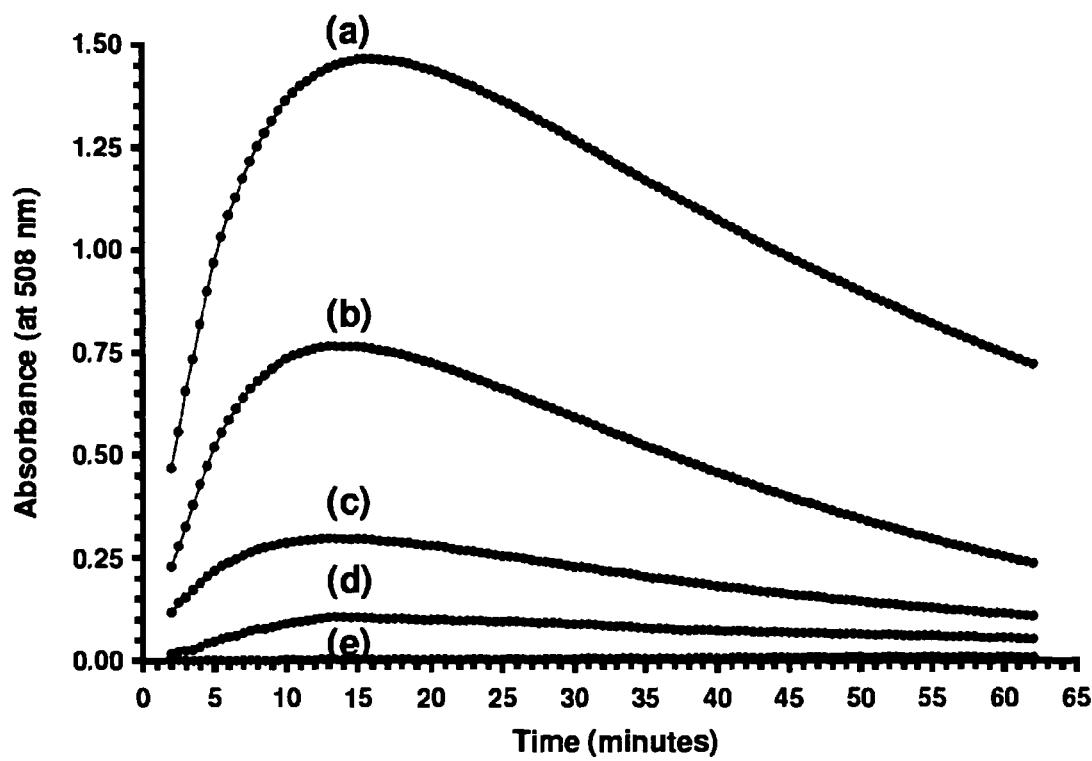
FIG. 6. Spectrophotometric assay 'timedrives' for cotinine standards ((a) 10 μg/mL; (b) 5 μg/mL; (c) 2 μg/mL; (d) 1 μg/mL; (e) 0 μg/mL (blank)) using barbituric acid (BA) as the chromophore-generating reagent (absorbance at 508 nm) (averaged results of triplicate analyses).
Figure 7:
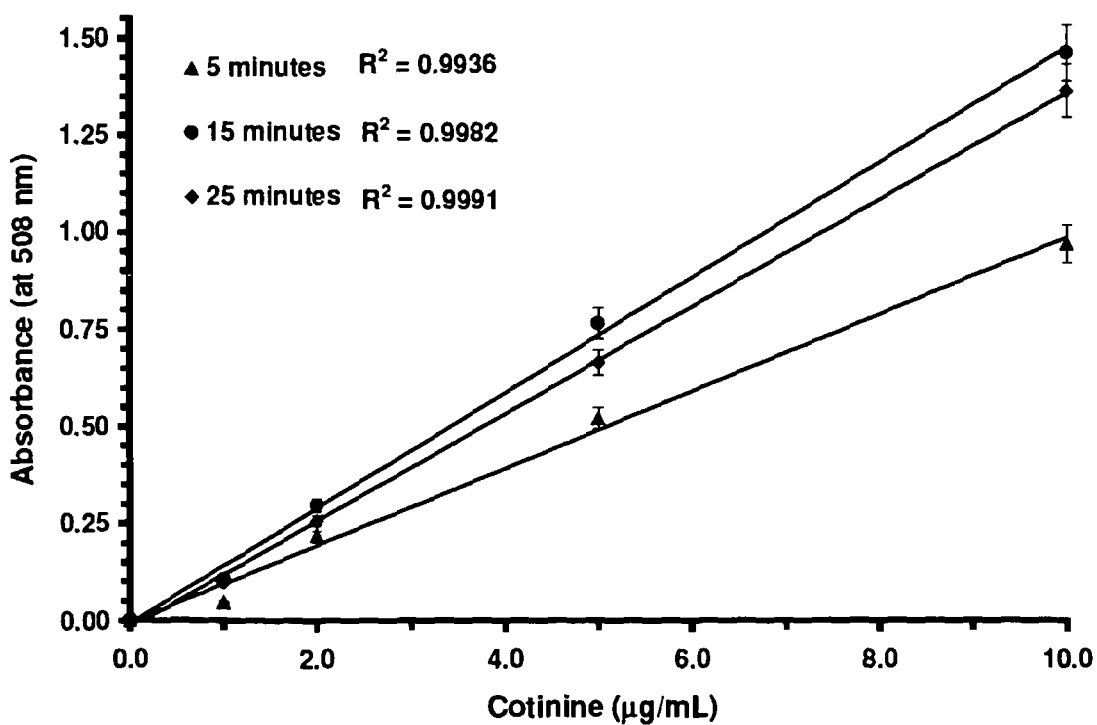
FIG. 7. Cotinine calibration curves (0-10 μg/mL) for the barbituric acid (BA) spectrophotometric assay using absorbance data (508 nm) collected after 5, 15, and 25 minutes.
Figure 8:
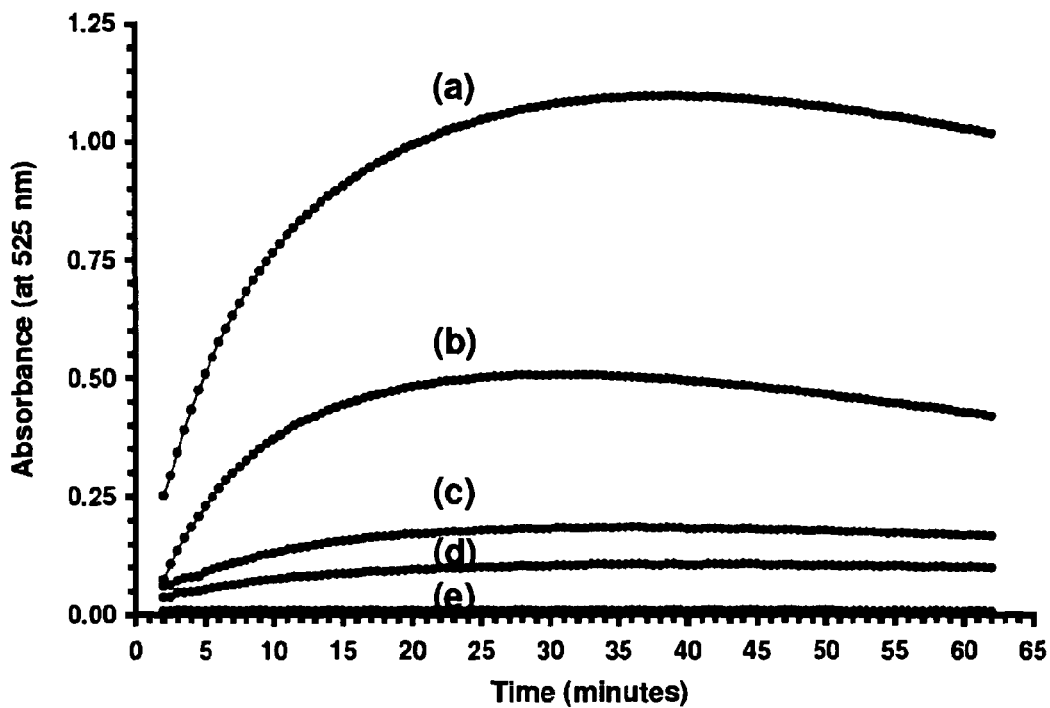
FIG. 8. Spectrophotometric assay 'timedrives' for cotinine standards ((a) 10 μg/mL; (b) 5 μg/mL; (c) 2 μg/mL; (d) 1 μg/mL; (e) 0 μg/mL (blank)) using 1,3-diethyl-2-thiobarbituric acid (DETBA) as the chromophore-generating reagent (absorbance at 525 nm) (averaged results of triplicate analyses).
Figure 9:
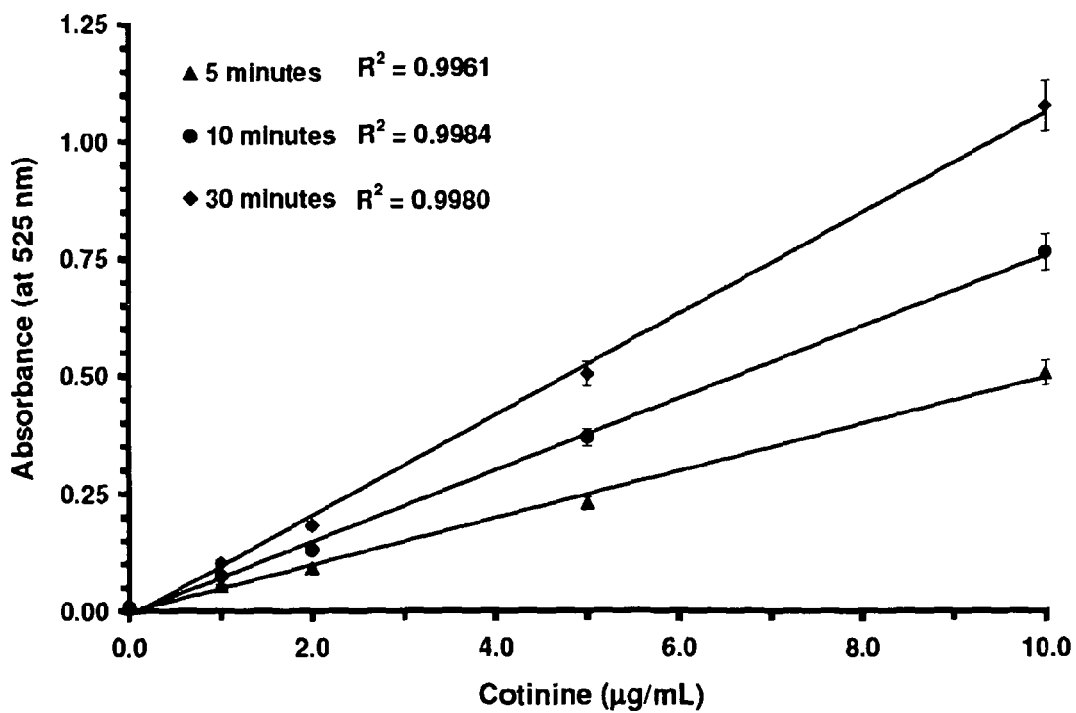
FIG. 9. Cotinine calibration curves (0-10 μg/mL) for the 1,3-diethyl-2-thiobarbituric acid (DETBA) spectrophotometric assay using absorbance data (525 nm) collected after 5, 10, and 30 minutes.
Figure 10:
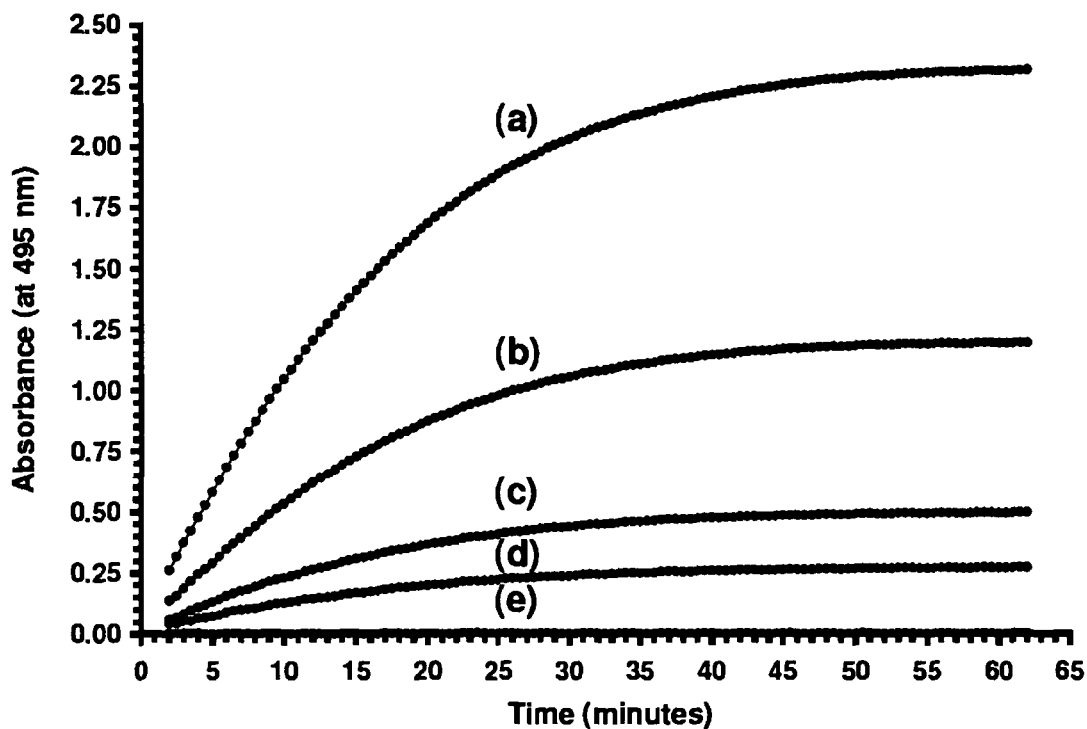
FIG. 10. Spectrophotometric assay 'timedrives' for cotinine standards ((a) 10 μg/mL; (b) 5 μg/mL; (c) 2 μg/mL; (d) 1 μg/mL; (e) 0 μg/mL (blank)) using Meldrum's acid (MA) as the chromophore-generating reagent (absorbance at 495 nm) (averaged results of triplicate analyses).
Figure 11:
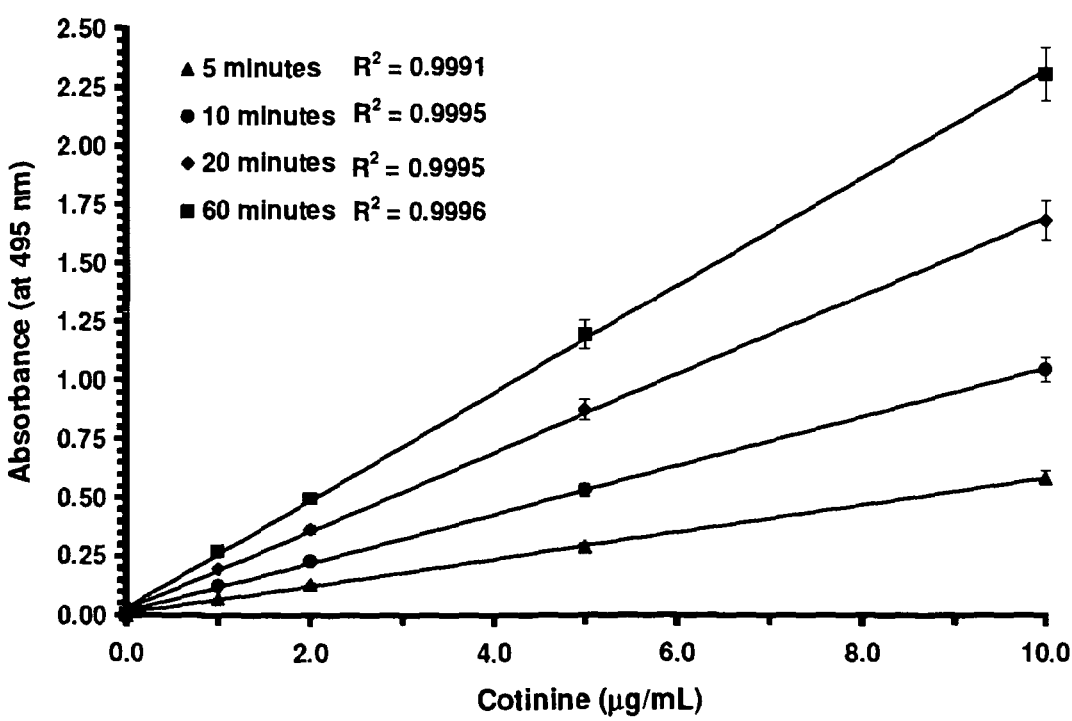
FIG. 11. Cotinine calibration curves (0-10 μg/mL) for the Meldrum's acid (MA) spectrophotometric assay using absorbance data (495 nm) collected after 5, 10, 20, and 60 minutes.
Figure 12:
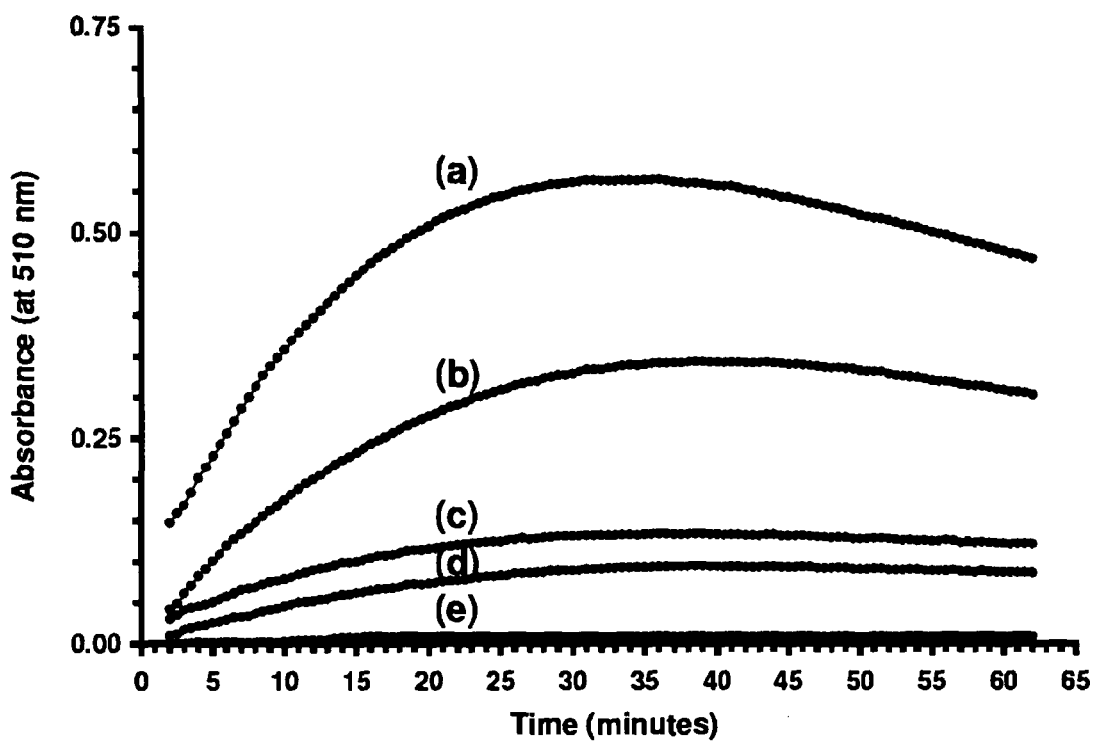
FIG. 12. Spectrophotometric assay 'timedrives' for cotinine standards ((a) 10 μg/mL; (b) 5 μg/mL; (c) 2 μg/mL; (d) 1 μg/mL; (e) 0 μg/mL (blank)) using 2-thiobarbituric acid (TBA) as the chromophore-generating reagent (absorbance at 510 nm) (averaged results of triplicate analyses).
Figure 13:
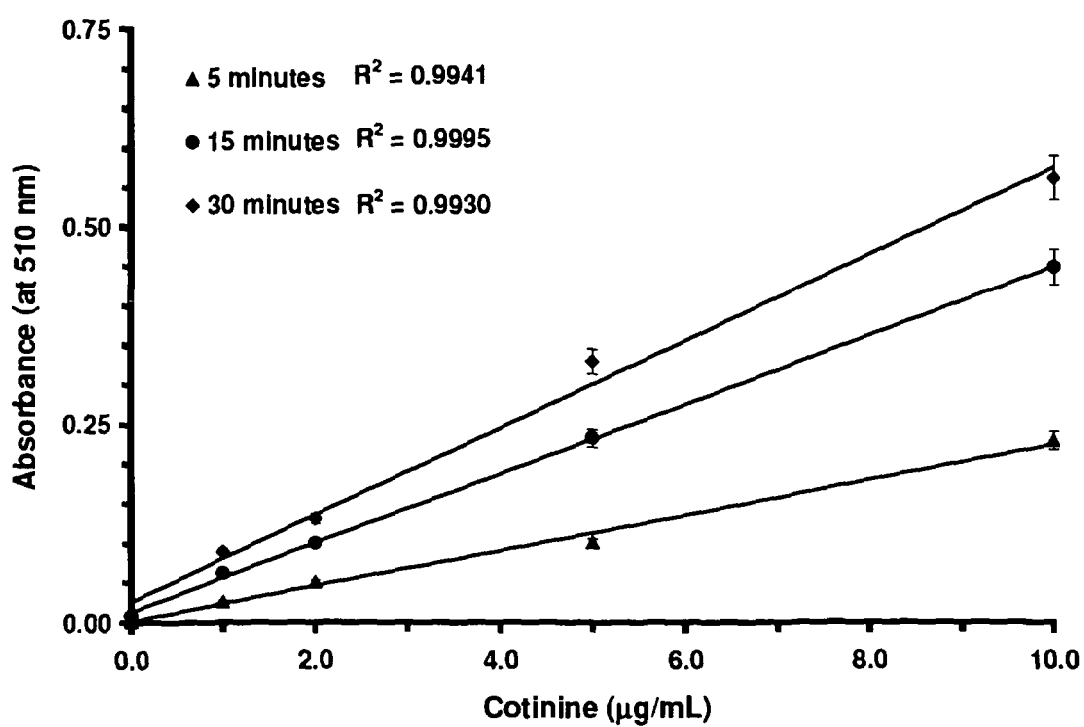
FIG. 13. Cotinine calibration curves (0-10 μg/mL) for the 2-thiobarbituric acid (TBA) spectrophotometric assay using absorbance data (510 nm) collected after 5, 15, and 30 minutes.

The wavelengths of maximum absorbance (lmax) when using barbituric acid (BA), 1,3-diethyl-2-thiobarbituric acid (DETBA), Meldrum's acid (MA), and 2-thiobarbituric acid (TBA), as the chromophore-generating reagents, were determined by performing wavescans on replicate solutions generated by spectrophotometric assay of cotinine standard solutions. Example absorbance spectra (400-600 nm) for BA (orange colour, lmax=508 nm) and DETBA (pink colour, lmax=525 nm), and MA (yellow colour, lmax=495 nm) and TBA (orange colour, lmax=510 nm), for specific cotinine concentrations and incubation times, are shown in FIGS. 4 and 5, respectively. From these wavescans it was provisionally estimated that in terms of response factor (absorbance units as a linear function of cotinine concentration) that MA>BA>DETBA>TBA. A range of cotinine standard solutions (10, 5, 2, 1 and 0 (blank) μg/mL) were assayed individually in triplicate using BA, DETBA, MA, and TBA as the chromophore-generating reagents, by timedrives (measuring absorbance at the reagent lmax as a function of incubation time, under ambient conditions) and averaged results are shown in FIGS. 6, 8, 10 and 12, respectively. From these timedrives, cotinine calibration curves (concentration versus absorbance) were constructed and linear regression analysis performed for specific incubation times (5, 10, 15, 20, 25, 30, 40, 50 and 60 minutes). Selected cotinine calibration curves for spectrophotometric assays performed in triplicate using BA, DETBA, MA, and TBA as the chromophore-generating reagents are displayed in FIGS. 7, 9, 11 and 13, respectively. In the case of BA, very good linearity (R values >0.998) was observed for incubation times in the region of 10-30 minutes (FIG. 7), with maximum absorbance occurring after ~13-16 minutes, followed by relatively rapid colour degradation, decreasing at a rate of −1%/minute over the next 20 minutes (FIG. 6). This allows single measurements (i.e. if not doing timedrives) to be taken within the 10-20 minute incubation window (i.e. the region of least rate of change of absorbance), so as to maximise response whilst minimising absorbance variation due to timing errors. With DETBA, very good linearity (R values >0.998) was observed for incubation times in the region of 5-40 minutes (FIG. 9), with maximum absorbance occurring after ~32-39 minutes, followed by relatively slow colour degradation, decreasing at a rate of <0.5%/minute over the next 20 minutes (FIG. 8). Single measurements can therefore be taken within the 20-40 minute incubation window. Using MA, excellent linearity (R values >0.999) was observed for incubation times over the entire tested region of 5-60 minutes (FIG. 11), with maximum absorbance not quite achieved even after 60 minutes (FIG. 10). Single measurements can therefore be taken at any specific time within the 5-60 minute incubation window. With TBA, very good linearity (R values >0.998) was only observed for incubation times in the region of 10-20 minutes (FIG. 13), with maximum absorbance occurring after ~35-40 minutes, followed by relatively slow colour degradation, decreasing at a rate of ~0.5%/minute over the next 20 minutes (FIG. 12). Single measurements can therefore be taken within the 10-20 minute incubation window.

The calibration curve equations determined by linear regression analysis of the absorbance versus cotinine concentration data for BA, DETBA, MA and TBA (measured at lmax for each reagent) at 5, 10, 15, 20, 25, 30, 40, 50 and 60 minutes incubation time were utilised to determine response factors (absorbance units per µg/mL cotinine concentration unit) for these chromophore-generating reagents under the employed assay conditions (detailed previously), which are shown in Table 1. Normalised against the response factor for DETBA, this shows that BA, MA and TBA are 1.4, 1.9 and 0.5 times as responsive, respectively (Table 1). Likewise, normalised against the response factor for MA, this shows that BA, DETBA and TBA are 0.7, 0.5 and 0.3 times as responsive, respectively (Table 1). Lower concentration cotinine standard solutions (in the range 0.2-1.0 µg/mL) were used in the assay to estimate the qualitative detection limit (limit of manual visual observance of a discernible colour compared with a reagent blank) and quantitative detection limit (limit of spectrophotometric ability to adequately distinguish between a standard and a reagent blank). These estimated detection limit values are shown in Table 1. Both qualitatively and quantitatively the sensitivity series is in the order MA>BA>DETBA≈TBA. However, spectrophotometric measurements can detect slightly lower levels than visual observation. This is of particular note with respect to MA, since low cotinine concentrations (very pale yellow colours) are difficult to distinguish by eye from the background (reagent blank).

TABLE 1

| | | Reagent solution (in d.i. water) | Response factor (abs. units per µg/mL cotinine) | Response factor (normalised against DETBA) | Response factor (normalised against MA) | Visual detection limit (µg/mL cotinine) | Spectrophotometric detection limit (µg/mL cotinine) |
|---|---|---|---|---|---|---|---|
| Comparative Example | 1 | BA | 0.126 | 1.4 | 0.7 | 0.8-1.0 | 06.-0.7 |
| | 2 | DETBA | 0.093 | 1.0 | 0.5 | ~1.0 | 0.5-1.0 |
| | 3 | MA | 0.181 | 1.9 | 1.0 | ~0.5* | 0.3-0.5 |
| | 4 | TBA | 0.047 | 0.5 | 0.3 | ~1.0 | 0.5-1.0 |
| Example | 1 | MPP | 0.180 | 1.9 | 1.0 | ~0.5 | 0.3-0.5 |
| | 2 | SPMP | 0.267 | 2.9 | 1.5 | ~0.3 | ~0.2 |
| | 3 | SPMP | 0.257 | 2.8 | 1.4 | ~0.2-0.3 | 0.1-0.2 |

*Low cotinine concentrations were difficult to detect visually with MA due to the pale yellow colour which can be difficult to distinguish from background.

From the wavescans (and comparison with the comparative examples) it can be seen that in terms of response factor (absorbance units as a linear function of cotinine concentration) SPMP>MPP≈MA>BA>DETBA>TBA.

Normalised against the response factor for DETBA, the results in table 1 show that MPP and SPMP are 1.9 and 2.9 times as responsive as DETBA, respectively. Likewise, normalised against the response factor for MA, the results in table 10 show that MPP and SPMP are 1.0 and 1.5 times as responsive as MA, respectively.

Normalised against the response factor for DETBA, SPMP (using cotinine-spiked NSS calibration) is 2.8 times as responsive (compared with 2.9 for SPMP using cotinine in deionised water calibration) (Table 1). Likewise, normalised against the response factor for MA, SPMP (using cotinine-spiked NSS calibration) is 1.4 times as responsive (compared with 1.5 for SPMP using cotinine in deionised water calibration) (Table 1). Thus the use of saliva has only a very small effect on the assay in terms of colour development using cotinine standards.

Both qualitatively and quantitatively the sensitivity series is in the order SPMP>MPP≈MA>BA>DETBA≈TBA, however, spectrophotometric measurements can detect lower levels than visual observation. Although the response factor of SPMP is slightly lower when using cotinine-spiked NSS, compared with cotinine in deionised water, it is possible to visually and spectrophotometrically, reproducibly discern slightly lower levels of cotinine.

Example 4

Aliquots of the supernatant from three centrifuged smoker's saliva samples (SS1-3) were subjected to triplicate analysis in the spectrophotometric assay using SPMP as the chromophore-generating reagent as in Example 3 above.

Figure 20:
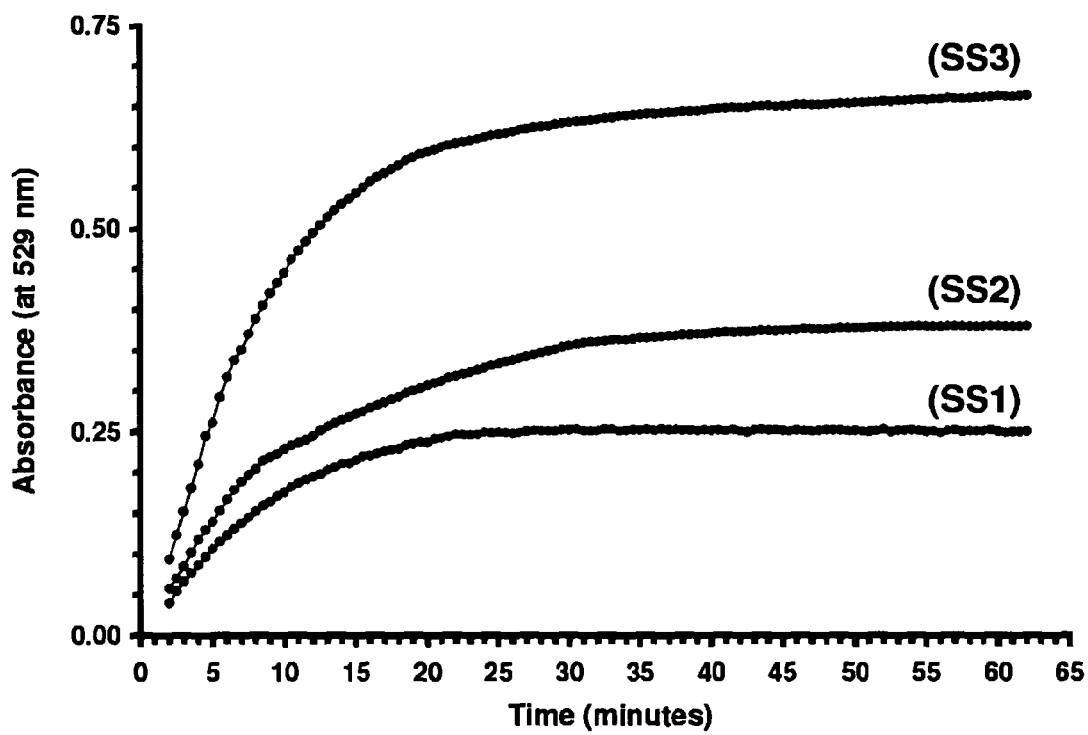
FIG. 20. Spectrophotometric assay 'timedrives' for smoker's saliva (SS) samples using 1-(4-sulfophenyl)-3-methyl-5-pyrazolone (SPMP) as the chromophoregenerating reagent (absorbance at 529 nm) (averaged results of triplicate analyses).

Timedrives (measuring absorbance at the reagent lmax as a function of incubation time, under ambient conditions) were performed, and averaged results are shown in FIG. 20.

The equivalent cotinine content of these saliva samples, as measured after incubation for specific times (namely 5, 10, 15, 20, 25, 30, 40, 50 and 60 minutes), was quantified using the corresponding incubation time SPMP/cotinine calibration curves for both cotinine in deionised water (FIG. 17) and cotinine-spiked NSS (FIG. 19). The results are presented in Table 2.

TABLE 2

| SS Sample | Self-reported smoking habit (cigarettes/day) | Cotinine equivalent (μg/mL from cotenine-spiked NSS calibration * | Cotinine equivalent (μg/mL) from cotenine/water calibration * |
|---|---|---|---|
| SS1 | <10 | 0.62 ± 0.06 (9%) | 0.83 ± 0.03 (4%) |
| SS2 | ~10 | 0.96 ± 0.02 (2%) | 1.13 ± 0.07 (6%) |
| SS3 | ~20 | 2.04 ± 0.19 (9%) | 2.08 ± 0.09 (5%) |

* Data is (mean ± standard deviation (% variation)) averaged over values obtained for 10, 15, 20, 25, 30, 40 and 50 minute incubation times using the corresponding cotinine calibration curves.
% variation = 100 × (standard deviation/mean)

The cotinine equivalents for the smoker's saliva sample correlate well with the self-reported smoking habits. Calibration with cotinine in deionised water gives slightly higher cotinine equivalent values compared with cotinine-spiked NSS calibration, however this is relatively insignificant with respect to rapid evaluation of smoking habits. It should be noted that the term 'cotinine equivalent' is used rather than cotinine when discussing the smoker's saliva samples since real samples will contain a large number of pyridine ring-containing nicotine metabolites (as detailed previously, and shown in FIG. 1), which will produce a range of slightly different chromophores in the assay (when using any of the chromophore-generating reagents). These chromophores may all have slightly different lmax wavelengths and response factors. Therefore measurement at a single wavelength and calibration with a single standard (cotinine) provides a value for total nicotine metabolites. However, this is better than techniques that specifically determine cotinine since they are more susceptible to fluctuations due to smoking frequency and an individuals metabolism with respect to nicotine breakdown.

Example 5

Based on the experiments in Example 2, a self-contained saliva testing kit was developed by incorporating the assay of Example 2 into a SafeTube® device but the buffer component was changed from acetate buffer (used in Example 2) to a citric acid/sodium citrate buffer system.

A citric acid/sodium citrate buffer was prepared by dissolving 2.7 g citric acid and 11.3 g sodium citrate in 100 ml of distilled/deionised water and dissolving 400 mg of SPMP into this solution. A 500 μl sample of this solution was dispensed into the bottom of individual SafeTube® reaction chambers. This 500 μl sample contains 56.6 mg sodium citrate, 13.5 mg citric acid and 2 mg SPMP.

1 g of potassium cyanide (KCN) was dissolved in 10 ml distilled/deionised water and 50 μl of the solution was dispensed into a (white) annulus assembly of the SafeTube® device providing 10 mg of KCN. This annulus assembly provides a separate chamber in which the KCN solution is kept separate from the SPMP/buffer solution in the reaction chamber of the SafeTube® device.

1 g of chloramine-T hydrate was dissolved in 10 ml distilled/deionised water and 50 μl of the solution was dispensed into a separate (pink) annulus assembly of the SafeTube® device providing 10 mg of chloramine-T hydrate. This annulus assembly provides a separate chamber in which the chloramine-T solution is kept separate from the SPMP/buffer solution in the reaction chamber and also separate from the KCN solution in the other annulus assembly of the SafeTube® device.

Figure 21:
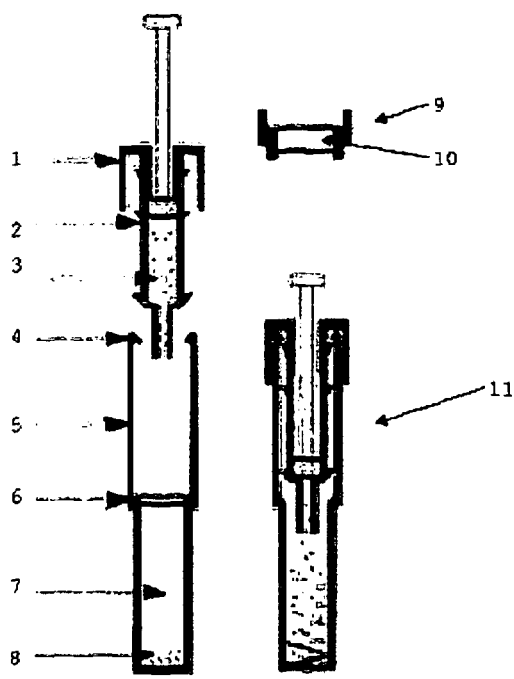
FIG. 21. shows a diagram of a SafeTube® device containing reagents for a point-of-care assay for nicotine metabolites as described in Example 5.

The general arrangement of reagents in the SafeTube® device is shown in FIG. 21. The dehydrated SPMP and buffer components 8 are in the reaction chamber 7 of the device. The membrane seal component 6 incorporates one or more stacked annulus units 9 which comprises two membranes defining a space 10 between them. The KCN component and the chloramine-T component are placed respectively into this space in two separate annulus components which are placed in the device at the membrane seal position 6. The fixed volume syringe 2 is used to introduce the saliva test sample 3 by pushing the syringe unit 2 into the top of the barrel 5 of the device until the barbs 4 on the barrel interact with those under the cap 1 of the syringe component 2 thus sealing the syringe onto the barrel 5 and puncturing the membrane seal(s) 6 which releases the reagents from the annulus component(s) to mix with the reagent in the reaction chamber 8. The sample 3 is then injected into the reaction chamber 7 to perform the assay in the assembled device 11.

The SafeTube® reaction chamber and two annulus assemblies were then placed in a freeze drying apparatus to freeze dry the SPMP solution, KCN solution and Chloramine-T solution over-night. When completely dry the two annulus components containing the KCN and chloramine-T were placed one on top of the other inside the SafeTube® barrel, but away from the dried SPMP in the reaction chamber. This along with a fixed-volume syringe constitutes the final SPMP SmokeScreen test kit as shown in FIG. 21.

A saliva sample was collected using a small sponge on a plastic handle, which when saturated with saliva holds approximately 1.5 ml. This was squeezed into a collecting bottle. The saliva sample was taken-up into the fixed-volume syringe from the SafeTube® kit and introduced onto the dried reagents. The saliva sample re-dissolved the solid KCN, chloramine-T and SPMP/buffer components to form a reaction mixture in the reaction vessel of the SafeTube® device.

The reaction mixture turned pink if cotinine was present in the sample. The reaction was very fast largely due to the use of dried reagents. With a saliva sample from a moderate smoker the sample turned pink within 1 minute and the final colour was present by 4 minutes. The test result (i.e. amount of cotinine present in the sample) was determined by comparison of the colour intensity with a standardised colour chart but as an alternative, a photometric analysis technique could be used to provide a quantitative result without requiring standardised colours for comparison.

The invention claimed is:

1. A method of detecting or measuring a nicotine metabolite in a sample comprising contacting the sample with a cyanogen halide and a pyrazolone compound and detecting a change in light absorbance of the pyrazolone compound; wherein the pyrazolone compound is a compound according to formula I

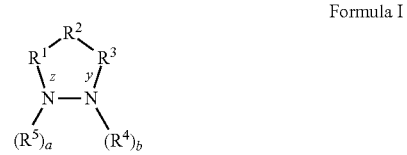

Formula I in which:
R$^1$ is —C(=O)—;
R$^2$ is —CH$_2$—;
R$^3$ is —C(R$^6$)—;
R$^5$ is phenyl substituted with —S(=O)$_2$OH;
R$^6$ is C$_{1-6}$alkyl;
z is a single bond and a is 1; and
y is a double bond and b is 0.

2. A method according to claim 1, wherein the pyrazolone compound has formula III

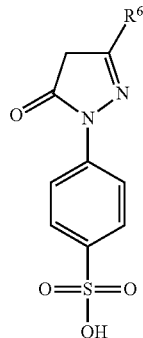

III

3. A method according to claim 1, wherein the pyrazolone compound is 1-(4-sulfophenyl)-3-methyl-5-pyrazolone (SPMP).

4. A method according to claim 1, wherein the cyanogen halide is cyanogen chloride.

5. A method according to claim 1, wherein the change in light absorbance is quantitatively correlated to the level of nicotine metabolite in the sample.

6. A kit for detection or measurement of a nicotine metabolite in a sample, the kit comprising:
a cyanogen halide or cyanogen halide-precursor(s); and
a pyrazolone compound as defined in claim 1.

7. A kit according to claim 6, comprising reagents KCN, chloramine-T and SPMP.

8. A kit according to claim 7, wherein the reagents of KCN, chloramine-T and SPMP are present in a KCN:chloramine-T:SPMP ratio of about 1:1:0.2 w/w.

* * * * *